United States Patent
Han et al.

(10) Patent No.: US 9,887,370 B2
(45) Date of Patent: Feb. 6, 2018

(54) COMPOUND FOR ORGANIC PHOTOELECTRIC DEVICE AND ORGANIC PHOTOELECTRIC DEVICE IMAGE SENSOR, AND ELECTRONIC DEVICE INCLUDING THE SAME

(71) Applicant: Samsung Electronics Co., Ltd., Suwon-si, Gyeonggi-do (KR)

(72) Inventors: Moon Gyu Han, Suwon-si (KR); Sakurai Rie, Suwon-si (KR); Sung Young Yun, Suwon-si (KR); Seon-Jeong Lim, Yongin-si (KR); Takkyun Ro, Hwaseong-si (KR); Gae Hwang Lee, Seongnam-si (KR); Tadao Yagi, Hwaseong-si (KR); Kyung Bae Park, Hwaseong-si (KR); Dong-Seok Leem, Hwaseong-si (KR); Yong Wan Jin, Seoul (KR); Chul-Joon Heo, Busan (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 14/974,485

(22) Filed: Dec. 18, 2015

(65) Prior Publication Data
US 2016/0181547 A1 Jun. 23, 2016

(30) Foreign Application Priority Data

Dec. 19, 2014 (KR) .......... 10-2014-0184627
Dec. 15, 2015 (KR) .......... 10-2015-0179513

(51) Int. Cl.
*H01L 51/00* (2006.01)
*H01L 27/30* (2006.01)
(Continued)

(52) U.S. Cl.
CPC ........ *H01L 51/0072* (2013.01); *C07D 455/04* (2013.01); *C07D 471/06* (2013.01);
(Continued)

(58) Field of Classification Search
CPC ............... C07D 455/04; C07D 471/06; H01L 27/14665; H01L 51/0072; H01L 51/424;
(Continued)

(56) References Cited

U.S. PATENT DOCUMENTS

| 4,921,827 A | 5/1990 | Ali et al. |
| 5,670,090 A * | 9/1997 | Marder ......... B82Y 30/00 252/582 |

(Continued)

FOREIGN PATENT DOCUMENTS

| CN | 101689610 A | 3/2009 |
| DE | 10343236 A1 | 4/2005 |

(Continued)

OTHER PUBLICATIONS

European Search Report dated Jun. 2, 2016 for corresponding European Patent Application No. 15200739.9.
(Continued)

*Primary Examiner* — Caridad Everhart
(74) *Attorney, Agent, or Firm* — Harness, Dickey & Pierce

(57) ABSTRACT

A compound is represented by Chemical Formula 1, an organic photoelectric device includes a first electrode and a second electrode facing each other and an active layer between the first electrode and the second electrode and including the compound represented by Chemical Formula 1, and an image sensor and an electronic device include the organic photoelectric device.

24 Claims, 11 Drawing Sheets

(51) Int. Cl.
*C07D 455/04* (2006.01)
*C07D 471/06* (2006.01)
*H01L 51/42* (2006.01)

(52) U.S. Cl.
CPC ........ *H01L 27/307* (2013.01); *H01L 51/0046* (2013.01); *H01L 51/0052* (2013.01); *H01L 51/0053* (2013.01); *H01L 51/0059* (2013.01); *H01L 51/0074* (2013.01); *H01L 51/0094* (2013.01); *H01L 51/424* (2013.01); *H01L 51/4253* (2013.01); *H01L 2251/308* (2013.01)

(58) Field of Classification Search
CPC ............. H01L 51/4253; H01L 51/0046; H01L 51/0059; H01L 51/0071; H01L 51/0094; H01L 51/0052; H01L 51/0053; H01L 27/307; H01L 2251/308
See application file for complete search history.

(56) References Cited

U.S. PATENT DOCUMENTS

| | | | |
|---|---|---|---|
| 5,721,288 | A | 2/1998 | Aotani et al. |
| 6,300,612 | B1 | 10/2001 | Yu |
| 6,303,943 | B1* | 10/2001 | Yu .......................... B82Y 10/00 257/40 |
| 7,129,466 | B2 | 10/2006 | Iwasaki |
| 7,847,364 | B2 | 12/2010 | Chen et al. |
| 7,973,307 | B2 | 7/2011 | Rand et al. |
| 8,035,708 | B2 | 10/2011 | Takizawa et al. |
| 8,242,493 | B2 | 8/2012 | Rand et al. |
| 8,338,691 | B2 | 12/2012 | Mitsui et al. |
| 8,426,727 | B2 | 4/2013 | Pfeiffer et al. |
| 8,525,577 | B2 | 9/2013 | Yofu et al. |
| 8,686,408 | B2 | 4/2014 | Yofu et al. |
| 2004/0086748 | A1 | 5/2004 | Nii et al. |
| 2005/0065351 | A1 | 3/2005 | Nii et al. |
| 2005/0267283 | A1 | 12/2005 | Weaver et al. |
| 2007/0012955 | A1 | 1/2007 | Ihama |
| 2007/0272918 | A1 | 11/2007 | Rand et al. |
| 2009/0014825 | A1* | 1/2009 | Chen .................. H01L 51/0097 257/433 |
| 2009/0223566 | A1 | 9/2009 | Mitsui et al. |
| 2010/0025665 | A1* | 2/2010 | Rand .................. H01L 51/0078 257/40 |
| 2011/0030801 | A1 | 2/2011 | Ikeda et al. |
| 2011/0031446 | A1 | 2/2011 | Ikeda et al. |
| 2013/0015435 | A1 | 1/2013 | Sawaki et al. |
| 2013/0181202 | A1 | 7/2013 | Yofu et al. |
| 2015/0340634 | A1* | 11/2015 | Forrest .................. B82Y 10/00 136/255 |
| 2017/0054089 | A1* | 2/2017 | Obana ................. H01L 51/0078 |

FOREIGN PATENT DOCUMENTS

| | | |
|---|---|---|
| EP | 469528 A1 | 2/1992 |
| EP | 0529162 A1 | 3/1993 |
| EP | 726497 A2 | 8/1996 |
| EP | 1445769 A1 | 8/2004 |
| EP | 2259359 A2 | 12/2010 |
| JP | H-0643641 A | 2/1994 |
| JP | 8-314139 | 11/1996 |
| JP | 2000-297068 A | 10/2000 |
| JP | 2005-019250 A | 1/2005 |
| JP | H-5210240 B2 | 6/2013 |
| KR | 2011-0104912 A | 9/2011 |
| WO | WO-2003-005481 | 1/2003 |
| WO | WO 2011-118578 A1 | 9/2011 |
| WO | WO-2012-032990 A1 | 3/2012 |
| WO | WO 2014-054255 A1 | 4/2014 |

OTHER PUBLICATIONS

Cheval, N. et al., "Assembly of poly-3-Hexylthiophene nano-crystallites into low dimensional structures using indandione derivatives," Nanomaterials, vol. 3, Feb. 1, 2013, pp. 107-116, XP002757450.

Berger, S.T.A. et al., "Electrophilicity parameters for 2-benzylidene-indan-1, 3-diones-a systematic extension of the benzhydrylium based electrophilicity scale," Organic & Biomolecular Chemistry, vol. 5, No. 8, Jan. 1, 2007, p. 3020, XP55271010.

Belyakov, S. et al., "2-(4,5,6,7,8,9-Hexahydro-6a-azaphenylen-2-ylmethylene) indan-1,3-dione," Acta Crystallographica Section E, vol. E4, No. o1200, May 29, 2009, XP002757445.

Blanchard-Desce, M., et al., "Large Quadratic Hyperpolarizabilities with Donor-Acceptor Polyenes Exhibiting Optimum Bond Length Alternation: Correlation between Structure and Hyperpolarizability," Chemistry European Journal, vol. 3, No. 7, 1997, pp. 1091-1104.

Marder, S. R., et al., "Large First Hyperpolarizabilities in Push-Pull Polyenes by Tuning of the Bond Length Alternation and Aromaticity," Science, vol. 263, Jan. 28, 1994, pp. 511-514.

Chinese Office Action dated Oct. 9, 2017 issued in corresponding Chinese Application No. 20150958624.9 (with translation).

Toshiyuki Urano et al., "Photosensitization Mechanisms in Photopolymer Coating Film Containing Photoinitiators Sensitized by Aminochalcone-type Dye for Cornputer-to-photopolymer Plate", Apr. 24, 1949, Polym. Adv. Technol., 10, 244-250.

STN-Registry RN-135838-93-6, Sep. 18, 2017, American Cancer Society.

STN-Registry RN-168845-06-5, Sep. 18, 2017, American Cancer Society.

* cited by examiner

COMPOUND FOR ORGANIC PHOTOELECTRIC DEVICE AND ORGANIC PHOTOELECTRIC DEVICE IMAGE SENSOR, AND ELECTRONIC DEVICE INCLUDING THE SAME

CROSS-REFERENCE TO RELATED APPLICATION

This application claims the benefit of priority from Korean Patent Application No. 10-2014-0184627, filed in the Korean Intellectual Property Office on Dec. 19, 2014 and Korean Patent Application No. 10-2015-0179513 filed on Dec. 15, 2015, the entire contents of which being incorporated herein by reference.

BACKGROUND

1. Field

Example embodiments relate to a compound for an organic photoelectric device, and an organic photoelectric device, an image sensor, and an electronic device including the same.

2. Description of the Related Art

A photoelectric device typically converts light into an electrical signal using photoelectric effects. The photoelectric device may include a photodiode, a phototransistor, and the like, and it may be applied to an image sensor, an organic light emitting diode, and the like.

An image sensor including a photodiode may require high resolution and thus a small pixel. At present, silicon photodiodes are widely used, but may exhibit the disadvantage of deteriorated sensitivity since silicon photodiode has a smaller absorption area due to small pixels. Accordingly, an organic material that is capable of replacing silicon has been researched.

Organic materials may have a high extinction coefficient and selectively absorb light in a particular wavelength region depending on a molecular structure, and thus may simultaneously replace a photodiode and a color filter and, as a result, improve sensitivity and contribute to high integration.

SUMMARY

Example embodiments relate to a compound for an organic photoelectric device being capable of selectively absorbing light in a green wavelength region and having improved thermal stability.

Example embodiments also relate to an organic photoelectric device being capable of selectively absorbing light in a green wavelength region and improving efficiency.

Example embodiments also relate to an image sensor and an electronic device including the above compound for an organic photoelectric device.

According to example embodiments, a compound for an organic photoelectric device is represented by Chemical Formula 1.

[Chemical Formula 1]

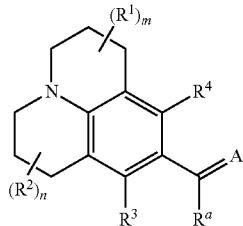

In Chemical Formula 1,

A is a functional group represented by Chemical Formula 1-1 or 1-2, $R^1$ to $R^4$ are independently one of hydrogen, a substituted or unsubstituted C1 to C30 alkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C2 to C30 heterocycloalkyl group, and a combination thereof, or two adjacent functional groups of $R^1$ to $R^4$ are linked to each other to provide a cycloalkyl group or a heterocycloalkyl group fused with a julolidinyl group, m and n are independently an integer ranging from 0 to 6, and $R^a$ is one of hydrogen, a substituted or unsubstituted C1 to C10 alkyl group, a substituted or unsubstituted C1 to C10 haloalkyl group, a halogen, a cyano group (—CN), and a combination thereof,

[Chemical Formula 1-1]

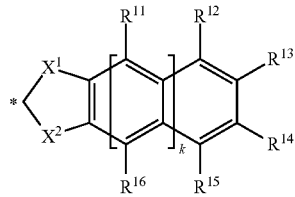

[Chemical Formula 1-2]

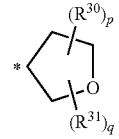

In Chemical Formulae 1-1 and 1-2, the asterisk (*) indicates a bonding position with a methine group of Chemical Formula 1, $X^1$ and $X^2$ are each independently —C($R^{22}$)($R^{23}$)— (wherein $R^{22}$ and $R^{23}$ are independently one of hydrogen, a substituted or unsubstituted C1 to C10 alkyl group, a substituted or unsubstituted C1 to C10 haloalkyl group, a halogen, a cyano group, a cyano-containing group, and a combination thereof), —C(=C($R^{24}$)($R^{25}$))— (wherein $R^{24}$ and $R^{25}$ are independently one of a substituted or unsubstituted C1 to C10 alkyl group, a substituted or unsubstituted C1 to C10 haloalkyl group, a halogen, a cyano group (—CN), a cyano-containing group, and a combination thereof), an indanone group, an indandione group, —C(=O)—, —S(=O)$_2$—, and a combination thereof, $R^{11}$ to $R^{16}$ are independently one of hydrogen, a substituted or unsubstituted C1 to C10 alkyl group, a substituted or unsubstituted C1 to C10 haloalkyl group, a halogen, a cyano group (—CN), a cyano-containing group, and a combination thereof, k is an integer of 0 or 1, $R^{30}$ is one of a halogen, a cyano group (—CN), a cyano-containing group, and a combination thereof, $R^{31}$ is one of hydrogen, a substituted or unsubstituted C1 to C10 alkyl group, a substituted or unsubstituted C1 to C10 haloalkyl group, a halogen, a cyano group (—CN), a cyano-containing group, and a combination thereof, p is an integer ranging from 1 to 5, q is an integer ranging from 0 to 5, and p+q is an integer of less than or equal to 5.

The compound represented by Chemical Formula 1 may include one aromatic ring in the fused ring moiety including a julolidinyl group of Chemical Formula 1.

The compound represented by Chemical Formula 1 may have 5 to 7 rings in total.

The compound represented by Chemical Formula 1 may have a maximum absorption wavelength ($\lambda_{max}$) of about 500 nm to about 600 nm, for example about 520 nm to about 570 nm in a thin film state.

The compound represented by Chemical Formula 1 may show a light absorption curve having a full width at half maximum (FWHM) of about 50 nm to about 100 nm in a thin film state.

$X^1$ and $X^2$ of Chemical Formula 1-1 may independently be —C($R^{22}$)($R^{23}$)— (wherein $R^{22}$ and $R^{23}$ are independently one of —F, —Cl, —Br, —I, a cyano group, a cyano-containing group, and a combination thereof), —C(=C($R^{24}$)($R^{25}$))— (wherein $R^{24}$ and $R^{25}$ are independently one of —F, —Cl, —Br, —I, a cyano group (—CN), a cyano-containing group, and a combination thereof), —C(=O)—, —S(=O)$_2$—, and combination thereof.

The A of Chemical Formula 1 may be a functional group represented by Chemical Formula 1A:

[Chemical Formula 1A]

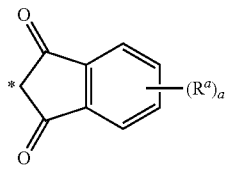

(1)

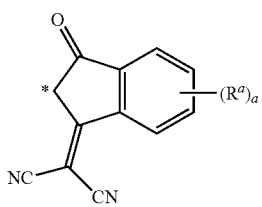

(2)

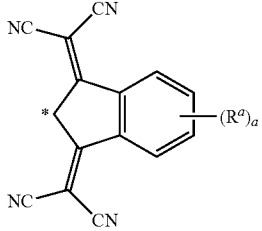

(3)

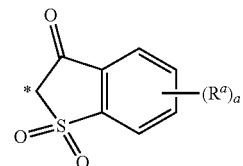

(4)

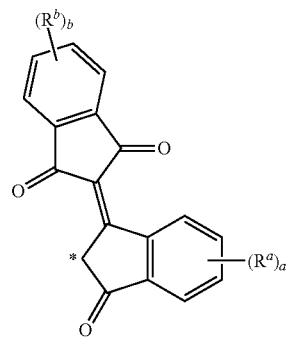

(5)

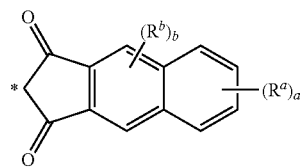

(6)

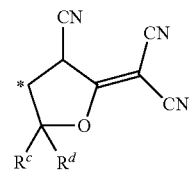

(7)

In Chemical Formula 1A, the asterisk (*) indicates a bonding position with a methine group of Chemical Formula 1, $R^a$, $R^b$, $R^c$, and $R^d$ are independently one of hydrogen, a substituted or unsubstituted C1 to C6 alkyl group, a substituted or unsubstituted C1 to C6 haloalkyl group, a halogen, a cyano group (—CN), a cyano-containing group, and a combination thereof, a is an integer ranging from 0 to 4, and b is an integer ranging from 0 to 2.

A compound for an organic photoelectric device represented by Chemical Formula 2 and having a maximum absorption wavelength ($\lambda_{max}$) of about 500 nm to about 600 nm in a thin film state is provided.

[Chemical Formula 2]

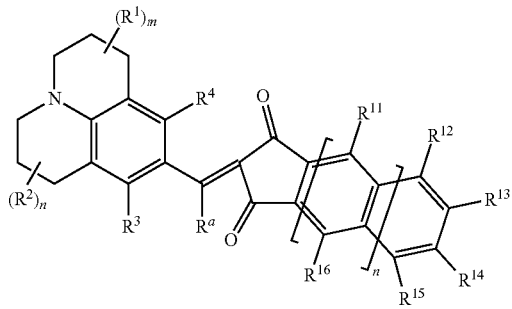

In Chemical Formula 2, $R^1$ to $R^4$ are independently one of hydrogen, a substituted or unsubstituted C1 to C30 alkyl group, a substituted or unsubstituted C6 to C30 aryl group, a substituted or unsubstituted C2 to C30 heteroaryl group, a substituted or unsubstituted C3 to C30 cycloalkyl group substituted or unsubstituted C2 to C30 heterocycloalkyl group, and a combination thereof, or two adjacent functional groups of $R^1$ to $R^4$ are linked to each other to provide a cycloalkyl group or a heterocycloalkyl group fused with a julolidinyl group, m and n are independently an integer ranging from 0 to 6, $R^a$ is one of hydrogen, a substituted or unsubstituted C1 to C10 alkyl group, a substituted or unsubstituted C1 to C10 haloalkyl group, a halogen, a cyano group (—CN), and a combination thereof, $R^{11}$ to $R^{16}$ are independently one of hydrogen, a substituted or unsubstituted C1 to C10 alkyl group, a substituted or unsubstituted C1 to C10 haloalkyl group, a halogen, a cyano group (—CN), and a cyano-containing group, and n is an integer of 0 or 1.

The compound may include one aromatic ring in the fused ring moiety including a julolidinyl group of Chemical Formula 1.

The compound may have 5 to 7 rings in total.

The compound may have a maximum absorption wavelength ($\lambda_{max}$) of about 520 nm to about 570 nm in a thin film state.

The compound may show a light absorption curve having a full width at half maximum (FWHM) of about 50 nm to about 100 nm in a thin film state.

According to example embodiments, an organic photoelectric device includes a first electrode and a second electrode facing each other, and an active layer between the first electrode and the second electrode and including the compound represented by Chemical Formula 1.

The active layer may further include an n-type semiconductor compound.

The n-type semiconductor compound may include sub-phthalocyanine, a sub-phthalocyanine derivative, fullerene or a fullerene derivative, thiophene or a thiophene derivative, or a combination thereof.

The active layer may include an intrinsic layer including the compound represented by Chemical Formula 1 or Chemical Formula 2.

The active layer may include a p-type layer including the compound represented by Chemical Formula 1 or Chemical Formula 2.

The active layer may further include at least one of a p-type layer on one side of the intrinsic layer and an n-type layer on the other side of the intrinsic layer.

The active layer may further include a second p-type semiconductor compound configured to selectively absorb green light. The second p-type semiconductor compound may be represented by, or include, Chemical Formula 6.

[Chemical Formula 6]

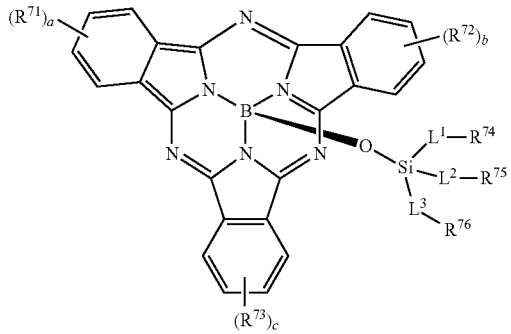

In Chemical Formula 6, $R^{71}$ to $R^{73}$ are independently one of hydrogen, a substituted or unsubstituted C1 to C30 aliphatic hydrocarbon group, a substituted or unsubstituted C6 to C30 aromatic hydrocarbon group, a substituted or unsubstituted C2 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group, or a combination thereof, or $R^{71}$ to $R^{73}$ are linked to each other to provide a fused ring, $L^1$ to $L^3$ are independently a single bond, a substituted or unsubstituted C1 to C30 alkylene group, a substituted or unsubstituted C6 to C30 arylene group, a divalent substituted or unsubstituted C2 to C30 heterocyclic group, or a combination thereof, $R^{74}$ to $R^{76}$ are independently a substituted or unsubstituted C1 to C30 alkyl group, a substituted or unsubstituted C6 to C30 aryl group, a substituted or unsubstituted C2 to C30 heterocyclic group, a substituted or unsubstituted C1 to C30 alkoxy group, a substituted or unsubstituted amine group, a substituted or unsubstituted silyl group, or a combination thereof, and a, b and c are independently an integer of 0 to 4.

When the active layer may include the compound and C60 in a volume ratio of about 0.9:1 to about 1.1:1, it may have an extinction coefficient of greater than or equal to about $8.0 \times 10^4$ cm$^{-1}$.

Example embodiments relate to an image sensor including the organic photoelectric device discussed above.

The image sensor may include a semiconductor substrate integrated with, or in combination with, a plurality of first photo-sensing devices sensing light in a blue wavelength region, a plurality of second photo-sensing devices sensing light in a red wavelength region, and the organic photoelectric device on the semiconductor substrate and selectively absorbing light in a green wavelength region.

The first photo-sensing device and the second photo-sensing device may be stacked in a vertical direction on the semiconductor substrate.

The image sensor may further include a color filter layer between the semiconductor substrate and the organic photoelectric device, and include a blue filter selectively transmitting light in a blue wavelength region and a red filter selectively transmitting light in a red wavelength region.

A green photoelectric device of the organic photoelectric device, a blue photoelectric device selectively absorbing light in a blue wavelength region, and a red photoelectric device selectively absorbing light in a red wavelength region may be stacked.

According to example embodiments, an electronic device including the image sensor is provided.

According to example embodiments, a compound for an organic photoelectric device includes an electron donor moiety and an electron acceptor moiety, wherein a selectivity of the organic photoelectric device in a green wavelength region is increased by the electron donor moiety.

According to example embodiments, the compound comprises a molecule represented by Chemical Formula 1 discussed above, where A is the electron acceptor moiety and the electron donor moiety includes the julolidinyl group.

DETAILED DESCRIPTION

Figure 1:
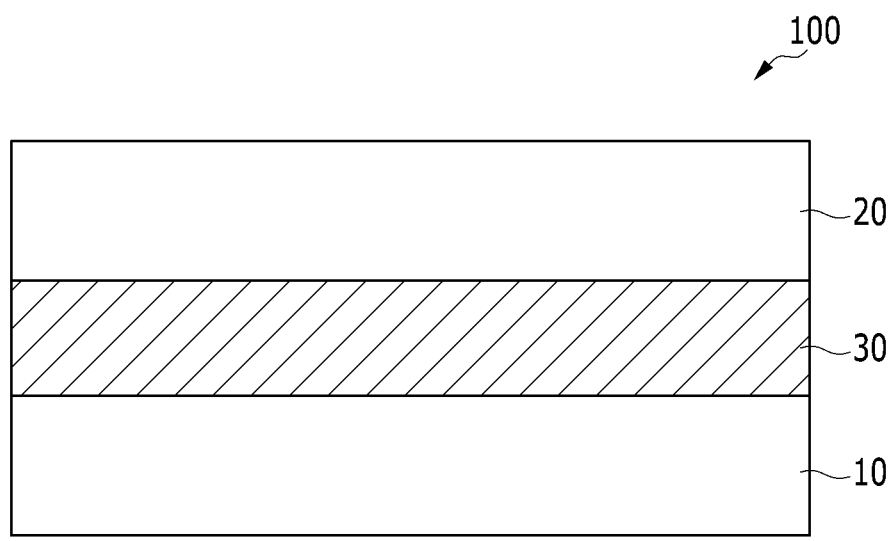
FIG. 1 is a cross-sectional view showing an organic photoelectric device according to example embodiments.

Example embodiments will hereinafter be described in detail, and may be more easily performed by those who have common knowledge in the related art. However, the example embodiments may be embodied in many different forms and are not construed as limited to the examples set forth herein.

In the drawings, the thickness of layers, films, panels, regions, etc., are exaggerated for clarity. Like reference numerals designate like elements throughout the specification.

It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the drawings, parts having no relationship with the description are omitted for clarity of the example embodiments, and the same or similar constituent elements are indicated by the same reference numerals throughout the specification.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

As used herein, when a definition is not otherwise provided, the term "substituted" refers to a functional group substituted with a substituent that is one of a halogen (F, Br, Cl or I), a nitro group, a cyano group, an amino group, an azido group, an amidino group, a hydrazino group, a hydrazono group, a carbonyl group, a carbamyl group, a thiol group, an ester group, a C1 to C20 alkyl group, a C2 to C20 alkenyl group, a C2 to C20 alkynyl group, a C1 to C20 alkoxy group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkynyl group, and a combination thereof, instead of hydrogen.

As used herein, when specific definition is not otherwise provided, the term "hetero" refers to one including 1 to 3 heteroatoms selected from N, O, S, P, and Si.

As used herein, when a definition is not otherwise provided, the "halogen" refers to F, Cl, Br, or I, and the "halogen-containing group" refers to a group where at least one hydrogen is substituted with F, Cl, Br, or I. For example, a haloalkyl group refers to an alkyl group where at least one hydrogen is substituted with F, Cl, Br, or I. Specific examples of the haloalkyl group may be a fluoroalkyl group, for example a perfluoroalkyl group.

As used herein, when a definition is not otherwise provided, the term "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as a dicyanoalkenyl group represented by $=CR^{x'}-(CR^{x}R^{y})_{p}-CR^{y'}(CN)_{2}$ wherein $R^{x}$, $R^{y}$, $R^{x'}$ and $R^{y'}$ are independently hydrogen or a C1 to C10 alkyl group, and p is an integer ranging from 0 to 10. Specific examples of the cyano-containing group may be a dicyanomethyl group, a dicyanovinyl group, a cyanoethynyl group, and the like.

As used herein, when a definition is not otherwise provided, the term "combination thereof" refers to at least two substituents bound to each other by a single bond or a C1 to C10 alkylene group, or at least two fused substituents. The haloalkyl group may be a C1 to C30 haloalkyl group (e.g., perfluoroalkyl group).

Hereinafter, a compound for an organic photoelectric device according to example embodiments is described.

A compound for an organic photoelectric device according to example embodiments is represented by Chemical Formula 1.

[Chemical Formula 1]

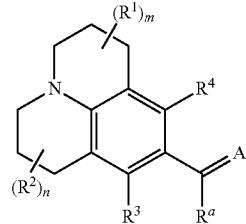

In Chemical Formula 1,

A is a functional group represented by Chemical Formula 1-1 or 1-2, $R^1$ to $R^4$ are independently one of hydrogen, a substituted or unsubstituted C1 to C30 alkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C2 to C30 heterocycloalkyl group, and a combination thereof, or two adjacent functional groups of $R^1$ to $R^4$ are linked to each other to provide a cycloalkyl group or a heterocycloalkyl group fused with a julolidinyl group, m and n are independently an integer ranging from 0 to 6, and $R^a$ is one of hydrogen, a substituted or unsubstituted C1 to C10 alkyl group, a substituted or unsubstituted C1 to C10 haloalkyl group, a halogen (—F, —Cl, —Br, or —I), a cyano group (—CN), and a combination thereof.

Two adjacent functional groups of $R^1$ to $R^4$ linked to each other to provide a cycloalkyl group or a heterocycloalkyl group fused with a julolidinyl group may be bonded to a different carbon.

In Chemical Formula 1, HOMO/LUMO energy levels, bandgap and absorbance of compounds may be controlled by introducing a substituent that is one of a substituted or unsubstituted C1 to C30 alkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C2 to C30 heterocycloalkyl group, and a combination thereof, at $R^1$ to $R^4$ positions. In example embodiments, the "substituted" may refer to one substituted with —F, —Cl, —Br, —I, a cyano group, a cyano-containing group, and a combination thereof.

In Chemical Formula 1, the julolidinyl group is a 2,3,6,7-tetrahydro-1H,5H-benzo[ij]quinolizinyl group that is an electron-donating functional group.

In Chemical Formula 1, the methine group is bonded in a para position (No. 9 position) with respect to N of the julolidinyl group and thus increases an electron donating function of the julolidinyl group.

In Chemical Formula 1, A is an electron withdrawing group and may be a functional group represented by Chemical Formula 1-1 or 1-2.

[Chemical Formula 1-1]

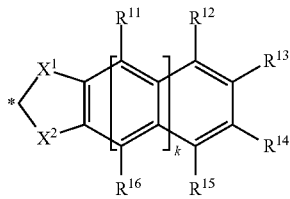

[Chemical Formula 1-2]

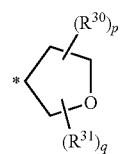

In Chemical Formulae 1-1 and 1-2, the asterisk (*) indicates a bonding position with a methine group of Chemical Formula 1, $X^1$ and $X^2$ are independently —C($R^{22}$)($R^{23}$)— (wherein $R^{22}$ and $R^{23}$ are independently one of hydrogen, a substituted or unsubstituted C1 to C10 alkyl group, a substituted or unsubstituted C1 to C10 haloalkyl group, a halogen, a cyano group, a cyano-containing group, and a combination thereof), —C(=C($R^{24}$)($R^{25}$))— (wherein $R^{24}$ and $R^{25}$ are independently one of a substituted or unsubstituted C1 to C10 alkyl group, a substituted or unsubstituted C1 to C10 haloalkyl group, a halogen, a cyano group (—CN), a cyano-containing group, and a combination thereof), an indanone group, an indandione group, —C(=O)—, —S(=O)$_2$—, and combination thereof, $R^{11}$ to $R^{16}$ are independently one of hydrogen, a substituted or unsubstituted C1 to C10 alkyl group, a substituted or unsubstituted C1 to C10 haloalkyl group, a halogen, a cyano group (—CN), a cyano-containing group, and a combination thereof, k is an integer of 0 or 1, $R^{30}$ is one of a halogen, a cyano group (—CN), a cyano-containing group, and a combination thereof, $R^{31}$ is one of hydrogen, a substituted or unsubstituted C1 to C10 alkyl group, a substituted or unsubstituted C1 to C10 haloalkyl group, a halogen, a cyano group (—CN), a cyano-containing group, and a combination thereof, p is an integer ranging from 1 to 5, q is an integer ranging from 0 to 5, and p+q is an integer of less than or equal to 5.

When the substituent $R^2$ at No. 7 carbon and the substituent $R^3$ at No. 8 carbon of Chemical Formula 1 are linked to each other to provide a cycloalkyl ring or a heterocycloalkyl ring fused with a benzene ring of the julolidinyl group, a full width at half maximum (FWHM) of a light absorption curve becomes narrower and wavelength selectivity is thus improved. Herein, the cycloalkyl ring refers to a C5 to C10 cycloalkyl ring and the heterocycloalkyl ring refers to a 5-membered to 10-membered heterocycloalkyl ring including at least one hetero atom selected from N, O, and S. The cycloalkyl ring or the heterocycloalkyl ring does not provide a conjugation structure with the benzene ring of the julolidinyl group. Thereby, selective absorption properties for green light may be improved. The compound for an organic photoelectric device includes an electron donor moiety and an electron acceptor moiety in the molecule, and thus has bipolar characteristics.

The compound for an organic photoelectric device may have 5 to 7 rings in total. Herein, the ring may be 5-membered to 10-membered rings as a closed structure. When the number of the ring is greater than 7, a maximum absorption wavelength is shifted toward red, and as a result selective absorption properties for green light may be deteriorated. In addition, when the number of the ring is less than 5, a maximum absorption wavelength is shifted toward blue, and thus selective absorption properties for green light may also be deteriorated.

The compound for an organic photoelectric device includes a bulky julolidinyl group as an electron donor moiety and decreases an intermolecular interaction among molecules in a film state, and thus reduces or substantially prevents unnecessary aggregation among the molecules. The aggregation among molecules causes a relatively wide absorption peak distribution. Accordingly, the compound for an organic photoelectric device may increase selectivity about a green wavelength region due to the electron donor moiety.

The compound may include one aromatic ring in the fused ring moiety including a julolidinyl group of Chemical Formula 1. Herein, the aromatic ring indicates a monocyclic ring or a polycyclic ring forming a valence electron conjugation structure inside the ring. In other words, two adjacent functional groups of $R^1$ to $R^4$ are linked to each other to provide a non-aromatic ring structure of a cycloalkyl group or a heterocycloalkyl group fused with a julolidinyl group. When the aromatic ring is greater than or equal to about two, a conjugation length is elongated, and thus green wavelength selectivity may not be provided, and absorption is also low.

The compound for an organic photoelectric device may show a light absorption curve having a relatively narrow full width at half maximum (FWHM) of about 50 nm to about 100 nm, for example about 50 nm to about 95 nm, or about 50 nm to about 90 nm in a thin film state. Herein, the FWHM is a width of a wavelength corresponding to half of the height at a maximum absorption point. As used herein, when specific definition is not otherwise provided, the FWHM may be defined by absorbance measured by UV-Vis spectroscopy. When the full width at half maximum (FWHM) is within the range of about 50 nm to about 100 nm, selectivity in a green wavelength region may be increased. The thin film may be a thin film deposited under a vacuum condition.

The compound for an organic photoelectric device is a compound selectively absorbing light in a green wavelength region, and may have a maximum absorption wavelength ($\lambda_{max}$) of about 500 nm to about 600 nm, for example about 520 nm to about 570 nm, or about 525 nm to about 570 nm in a thin film state.

The compound for an organic photoelectric device may have a HOMO level of about 5.2 eV to about 5.7 eV, and an LUMO level of about 3.2 eV to about 3.7 eV. The compound for an organic photoelectric device having the HOMO level and the LUMO level within the ranges may be used as a semiconductor effectively absorbing light in a green wavelength region, and thus has high external quantum efficiency (EQE), and as a result improves photoelectric conversion efficiency.

The compound for an organic photoelectric device may have a molecular weight of about 300 to about 900, for example about 350 to about 700. When the compound has a molecular weight within the above range, the crystallinity of the compound and thermal decomposition during formation of a thin film by deposition may be inhibited.

The compound for an organic photoelectric device may have a decomposition temperature that is greater than or equal to about 220° C., for example greater than or equal to about 250° C. Herein, the decomposition temperature may be regarded as a temperature at which a weight loss of the compound is about 1 wt %. As the compound for an organic photoelectric device has a higher decomposition temperature than the melting temperature of the compound, that is, as the melting temperature and the decomposition temperature have a larger difference, thermal stability during the deposition process is improved. When the melting point satisfies the range where the melting temperature is lower than the melting temperature, the compound may stably be deposited in a film state and reduce a decomposition product and as a result, provide an organic photoelectric device having improved photoelectric conversion performance.

$X^1$ and $X^2$ of Chemical Formula 1-1 may independently be —C($R^{22}$)($R^{23}$)— (wherein $R^{22}$ and $R^{23}$ are independently one of —F, —Cl, —Br, —I, a cyano group, a cyano-containing group, and a combination thereof), —C(=C($R^{24}$)($R^{25}$))— (wherein $R^{24}$ and $R^{25}$ are independently one of —F, —Cl, —Br, —I, a cyano group (—CN), a cyano-containing group, and a combination thereof), —C(=O)—, —S(=O)$_2$—, and a combination thereof.

Specific examples of "A" may be functional groups represented by Chemical Formula 1A (1) to (7).

[Chemical Formula 1A]

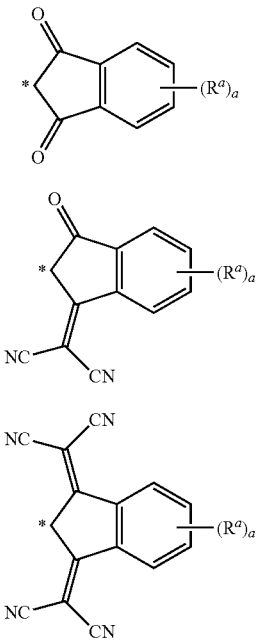

-continued

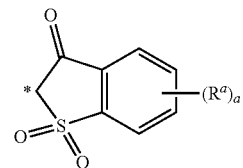

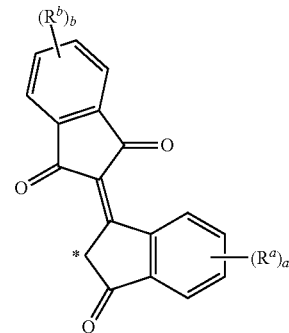

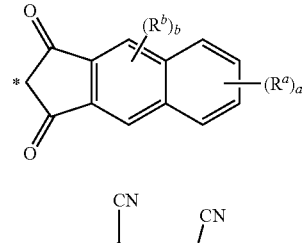

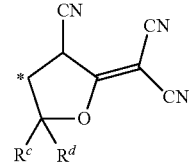

In Chemical Formula 1A,
the asterisk (*) indicates a bonding position with a methine group of Chemical Formula 1, $R^a$, $R^b$, $R^c$ and $R^d$ are independently one of hydrogen, a substituted or unsubstituted C1 to C6 alkyl group, a substituted or unsubstituted C1 to C6 haloalkyl group, a halogen, a cyano group (—CN), a cyano-containing group, and a combination thereof,
a is an integer ranging from 0 to 4, and b is an integer ranging from 0 to 2.

In the functional group of Chemical Formula 1A, the functional group represented by Chemical Formula 1A (1) may be a functional group represented by Chemical Formula 1A (8).

[Chemical Formula 1A (8)]

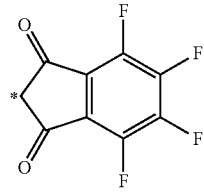

In Chemical Formula 1A (8),
the asterisk (*) indicates a bonding position with a methine group of Chemical Formula 1.

The compound for an organic photoelectric device may be represented by Chemical Formula 2.

[Chemical Formula 2]

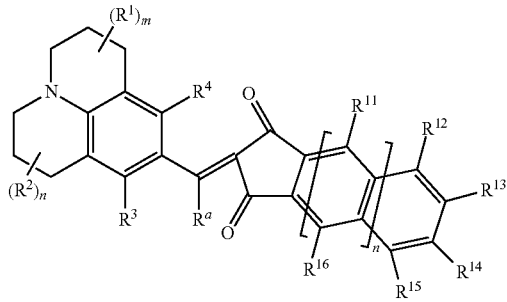

In Chemical Formula 2, $R^1$ to $R^4$ are independently at least one of hydrogen, a substituted or unsubstituted C1 to C30 alkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C2 to C30 heterocycloalkyl group, and a combination thereof, or two adjacent functional groups of $R^1$ to $R^4$ are linked to each other to provide a cycloalkyl group or a heterocycloalkyl group fused with a julolidinyl group, m and n are independently an integer ranging from 0 to 6, $R^a$ is one of hydrogen, a substituted or unsubstituted C1 to C10 alkyl group, a substituted or unsubstituted C1 to C10 haloalkyl group, a halogen, a cyano group (—CN), and a combination thereof, $R^{11}$ to $R^{16}$ are independently at least one of hydrogen, a substituted or unsubstituted C1 to C10 alkyl group, a substituted or unsubstituted C1 to C10 haloalkyl group, a halogen, a cyano group (—CN), a cyano-containing group, and a combination thereof, and n is an integer of 0 or 1.

Hereinafter, an organic photoelectric device including the compound according to example embodiments is described with reference to the following drawings.

FIG. 1 is a cross-sectional view showing an organic photoelectric device, according to example embodiments.

Referring to FIG. 1, an organic photoelectric device 100 according to example embodiments includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin monolayer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound for an organic photoelectric device represented by Chemical Formula 1 may be configured as a p-type semiconductor compound in the active layer 30.

The compound for an organic photoelectric device is a compound that selectively absorbs light in a green wavelength region, and the active layer 30 including the compound may have a maximum absorption wavelength ($\lambda_{max}$) in a wavelength region of about 500 nm to about 600 nm, for example about 520 nm to about 570 nm or 525 nm to about 570 nm.

The active layer 30 may exhibit a light absorption curve having a relatively narrow full width at half maximum (FWHM) of about 50 nm to about 100 nm, and specifically about 50 nm to about 90 nm. Accordingly, the active layer 30 has high selectivity for light in a green wavelength region.

The active layer 30 may further include an n-type semiconductor compound for forming a pn junction.

The n-type semiconductor compound may be sub-phthalocyanine or a sub-phthalocyanine derivative, fullerene or a fullerene derivative, thiophene or a thiophene derivative, or a combination thereof.

The fullerene may include fullerene C60, fullerene C70, fullerene C76, fullerene C78, fullerene C80, fullerene C82, fullerene C84, fullerene C90, fullerene C96, fullerene C240, fullerene C540, mixed fullerene, fullerene nanotube, etc. The "fullerene derivatives" may refer to compounds of these fullerenes having a substituent attached thereto. The fullerene derivatives may include substituents such as alkyl groups, aryl groups, or heterocyclic groups. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

The sub-phthalocyanine or sub-phthalocyanine derivative may be represented by Chemical Formula 3.

[Chemical Formula 3]

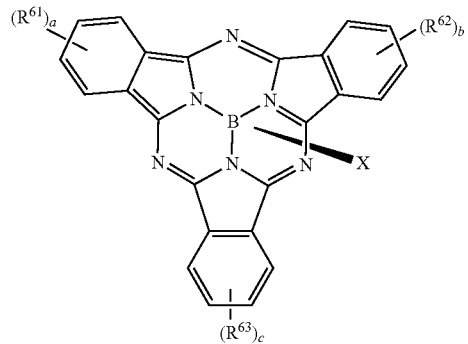

In Chemical Formula 3, $R^{61}$ to $R^{63}$ are independently hydrogen, a substituted or unsubstituted C1 to C30 alkyl group, a substituted or unsubstituted C6 to C30 aryl group, a substituted or unsubstituted C3 to C30 heteroaryl group, a halogen, a halogen-containing group, or a combination thereof, a, b, and c are integers ranging from 1 to 3, and X is a halogen, for example F or Cl.

The thiophene derivative may be, for example represented by Chemical Formula 4 or Chemical Formula 5, but is not limited thereto.

[Chemical Formula 4]

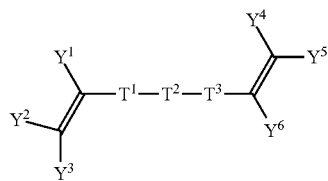

[Chemical Formula 5]

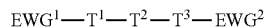

In Chemical Formulae 4 and 5, each of $T^1$, $T^2$, and $T^3$ is an aromatic ring including substituted or unsubstituted thiophene moieties, each of $T^1$, $T^2$, and $T^3$ is independently present or are fused to each other, each of $Y^1$ to $Y^6$ is independently hydrogen, a substituted or unsubstituted C1 to C30 alkyl group, a substituted or unsubstituted C6 to C30 aryl group, a substituted or unsubstituted C3 to C30 heterocyclic group, a cyano group, or a combination thereof, and each of $EWG^1$ and $EWG^2$ is independently electron withdrawing groups.

For example, in the Chemical Formula 4, at least one of $Y^1$ to $Y^6$ is an electron withdrawing group, for example a cyano group or a cyano-containing group.

The active layer 30 may further include a second p-type semiconductor compound selectively absorbing green light. The p-type semiconductor compound may be a compound represented by Chemical Formula 6.

[Chemical Formula 6]

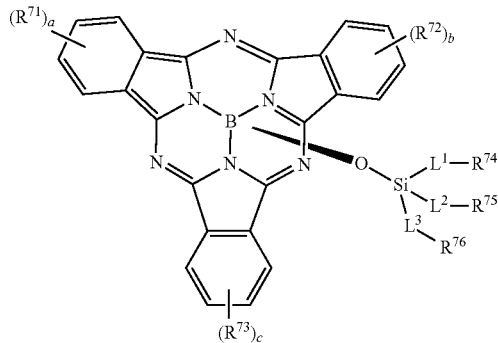

In Chemical Formula 6, $R^{71}$ to $R^{73}$ are independently hydrogen, a substituted or unsubstituted C1 to C30 aliphatic hydrocarbon group, a substituted or unsubstituted C6 to C30 aromatic hydrocarbon group, a substituted or unsubstituted C2 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or $R^{71}$ to $R^{73}$ are linked to each other to provide a fused ring, $L^1$ to $L^3$ are independently a single bond, a substituted or unsubstituted C1 to C30 alkylene group, a substituted or unsubstituted C6 to C30 arylene group, a divalent substituted or unsubstituted C2 to C30 heterocyclic group, or a combination thereof, $R^{74}$ to $R^{76}$ are independently a substituted or unsubstituted C1 to C30 alkyl group, a substituted or unsubstituted C6 to C30 aryl group, a substituted or unsubstituted C2 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a, b and c are independently an integer of 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a volume ratio of about 1:100 to about 100:1. The compound of Chemical Formula 1 and the n-type semiconductor compound may be included in a ratio ranging from about 1:50 to about 50:1 within the range, for example, about 1:10 to about 10:1, or about 1:1. When the compound of Chemical Formula 1 and the n-type semiconductor compound have a composition ratio within the range, an exciton may be effectively produced and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm, and specifically, about 5 nm to about 300 nm. When the active layer 30 has a thickness within the range, the active layer may effectively absorb light, effectively separate holes from electrons, and deliver them, thereby effectively improving photoelectronic conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90% or more.

The active layer 30 may be formed by depositing the compound for an organic photoelectric device and an n-type semiconductor compound, for example, C60 in a volume ratio of about 0.9:1 to about 1.1:1 and specifically, about 1:1 and have an extinction coefficient of greater than or equal to about $8.0 \times 10^4$ cm$^{-1}$ and specifically, greater than or equal to about $8.5 \times 10^4$ cm$^{-1}$. The active layer 30 having a high extinction coefficient as above may be formed to be very thin. The thin active layer 30 may narrow a gap between the first electrode 10 and the second electrode 20 and provide a thin organic photoelectric device and accordingly, the thin organic photoelectric device may be operated by a stronger electric field than a thicker organic photoelectric device when the same voltage is applied thereto. Herein, the thin organic photoelectric device may have higher efficiency.

In the organic photoelectric device 100, when light enters from the first electrode 10 and/or second electrode 20, and when the active layer 30 absorbs light having a desired, or alternatively predetermined wavelength, excitons may be produced from the inside. The excitons are separated into holes and electrons in the active layer 30, the separated holes are transported to an anode that is one of the first electrode 10 and second electrode 20, and the separated electrons are transported to the cathode that is the other of and the first electrode 10 and second electrode 20 so as to flow a current in the organic photoelectric device.

Hereinafter, an organic photoelectric device according to example embodiments is described with reference to FIG. 2.

Figure 2:
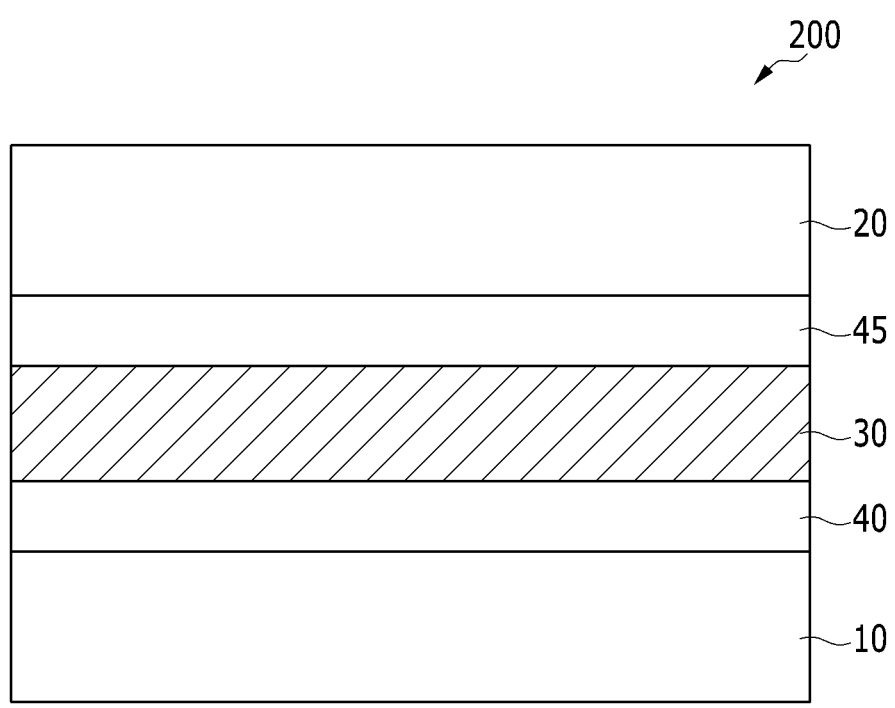
FIG. 2 is a cross-sectional view of an organic photoelectric device according to example embodiments.

FIG. 2 is a cross-sectional view of an organic photoelectric device, according to example embodiments.

Referring to FIG. 2, an organic photoelectric device 200, according to example embodiments includes a first electrode 10 and a second electrode 20 facing each other, and an active layer 30 between the first electrode 10 and the second electrode 20.

However, the organic photoelectric device 200 according to the example embodiments further includes charge auxiliary layers 40 and 45 between the first electrode 10 and the active layer 30, and between the second electrode 20 and the active layer 30, respectively. The charge auxiliary layers 40 and 45 may facilitate the transfer of holes and electrons separated from the active layer 30, so as to increase efficiency.

The charge auxiliary layers 40 and 45 may be at least one of a hole injection layer (HIL) for facilitating hole injection, a hole transport layer (HTL) for facilitating hole transport, an electron blocking layer (EBL) for reducing or substantially preventing electron transport, an electron injection layer (EIL) for facilitating electron injection, an electron transport layer (ETL) for facilitating electron transport, and a hole blocking layer (HBL) for reducing or substantially preventing hole transport.

The charge auxiliary layers 40 and 45 may include, for example, an organic material, an inorganic material, or a combination of an organic/inorganic material. The organic material may be an organic compound having hole or electron injection and/or transportation characteristics, and the inorganic material may be or include, for example, a metal oxide such as molybdenum oxide, tungsten oxide, nickel oxide, and the like.

The hole transport layer (HTL) may include one of, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one of, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one of, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

The hole blocking layer (HBL) may include one of, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

Either one of the charge auxiliary layers 40 and 45 may be omitted, according to various example embodiments.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
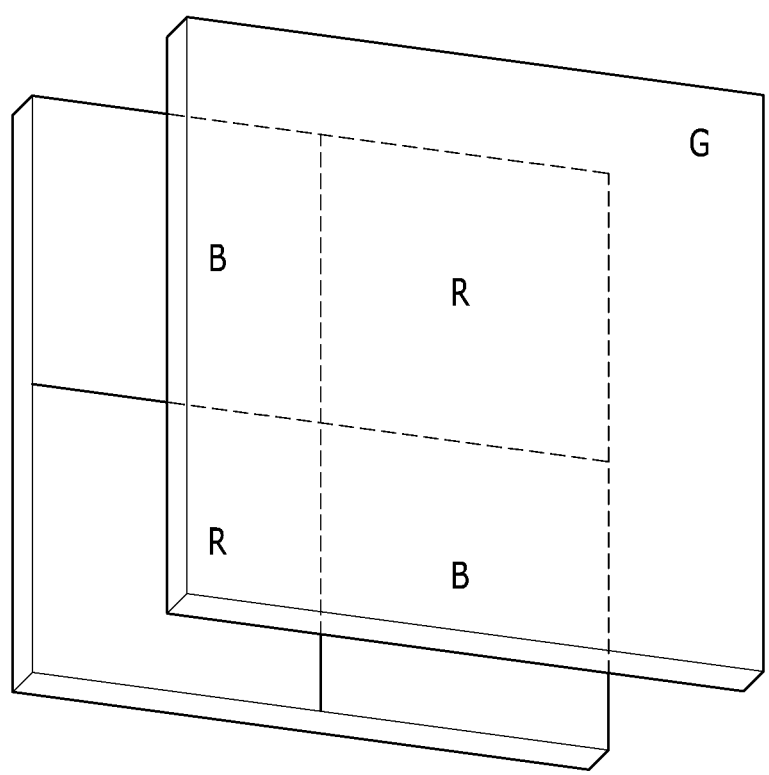
FIG. 3 is a schematic view showing an organic CMOS image sensor according to example embodiments.
Figure 4:
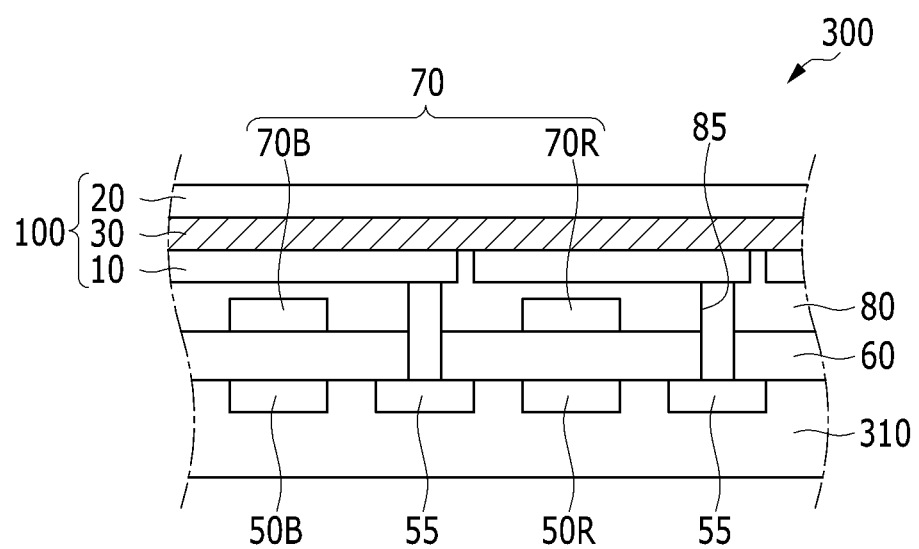
FIG. 4 is a cross-sectional view showing the organic CMOS image sensor of FIG. 3.

FIG. 3 is a schematic top plan view of an organic CMOS image sensor, according to example embodiments, and FIG. 4 is a cross-sectional view of the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage 55, a lower insulation layer 60, a color filter layer 70, an upper insulation layer 80, and an organic photoelectric device 100.

The semiconductor substrate 310 may be or include a silicon substrate, and may be integrated with the photo-sensing devices 50B and/or 50R, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel, and the charge storage 55 may be included in a green pixel.

The photo-sensing devices 50B and 50R may sense light, the information sensed by the photo-sensing devices 50B and 50R may be transferred by the transmission transistor to an image processor, the charge storage 55 is electrically connected with the organic photoelectric device 100, and the information of the charge storage 55 may be transferred by the transmission transistor to an image processor.

In the drawings, the photo-sensing devices 50B and 50R are, for example, arranged in parallel without limitation, however the blue photo-sensing device 50B and the red photo-sensing device 50R may also be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of or include an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

In the drawings, a color filter layer 70 is formed on the lower insulation layer 60. The color filter layer 70 may include a blue filter 70B formed in the blue pixel and selectively transmitting blue light, and a red filter 70R formed in the red pixel and selectively transmitting red light. In various example embodiments, a green filter may also be included.

In various example embodiments, the color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may be omitted.

In the drawings, the upper insulation layer 80 is formed on the color filter layer 70. The upper insulation layer 80 may reduce or eliminate a step caused by the color filter layer 70 and may smoothen the surface. The upper insulation layer 80 and the lower insulation layer 60 may also include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes. The active layer 30 selectively absorbs light in a green wavelength region and replaces a color filter of a green pixel.

When light enters from the second electrode 20, the light in a green wavelength region may be mainly absorbed in the active layer 30 and photoelectronically converted, while the light in the rest of the wavelength regions passes through first electrode 10 and may be sensed in the photo-sensing devices 50B and 50R.

The compound for an organic photoelectric device may be usefully applicable to an image sensor having a stacking structure shown in FIGS. 3 and 4 because the organic photoelectric device exhibits improved green selective absorption properties. As described above, the organic photoelectric devices selectively absorbing light in a green wavelength region are stacked, and thereby a size of an image sensor may be decreased and a down-sized image sensor may be realized.

Figure 5:
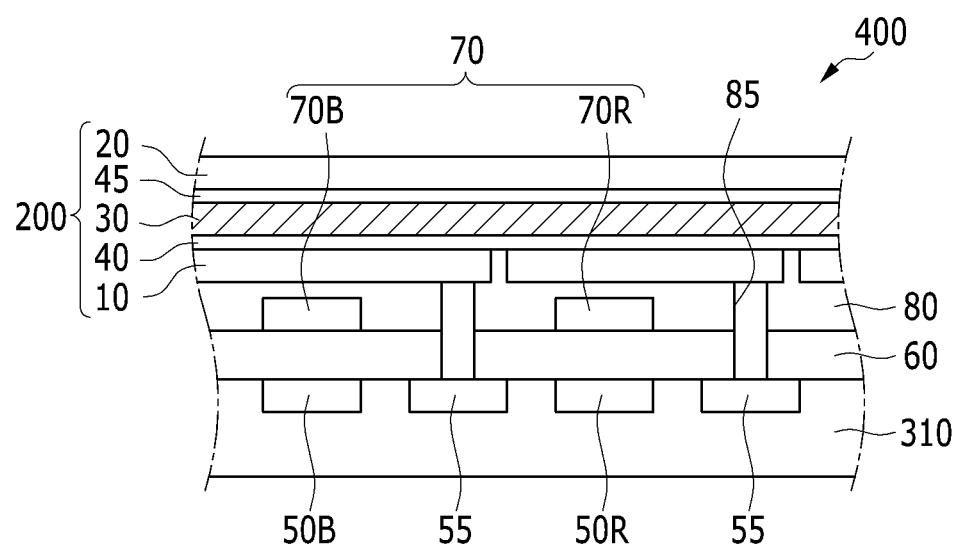
FIG. 5 is a schematic cross-sectional view showing an organic CMOS image sensor according to example embodiments.

In FIG. 4, the organic photoelectric device 100 of FIG. 1 is included, but it is not limited thereto, and thus the organic photoelectric device 200 of FIG. 2 may be similarly used. FIG. 5 shows a structure of an image sensor having the structure illustrated in FIG. 2, and is a cross-sectional view of an organic CMOS image sensor 400 including the organic photoelectric device 200 in FIG. 2.

Figure 6:
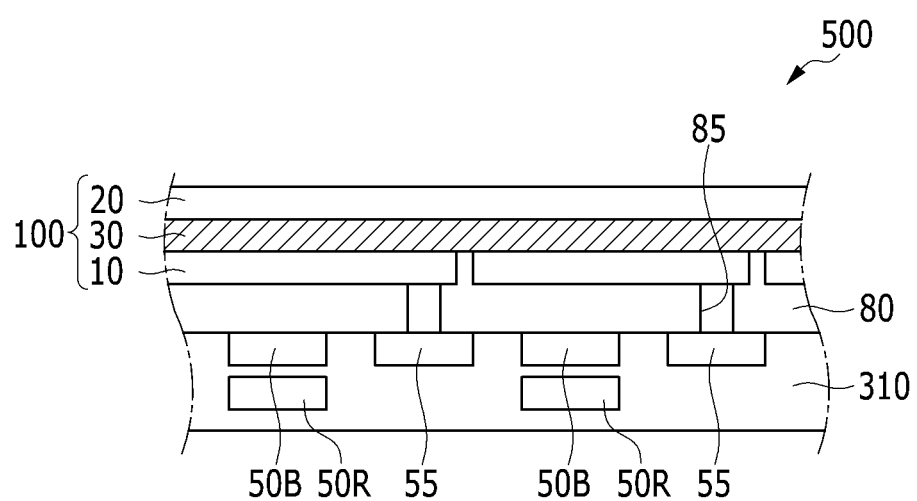
FIG. 6 is a schematic cross-sectional view showing an organic CMOS image sensor according to example embodiments.

FIG. 6 is a cross-sectional view showing the organic CMOS image sensor according to example embodiments.

Referring to FIG. 6, the organic CMOS image sensor 500 according to various example embodiments includes a semi-conductor substrate 310 integrated with photo-sensing devices 50B and 50R, a transmission transistor (not shown), a charge storage 55, an insulation layer 80, and an organic photoelectric device 100.

In example embodiments, the organic CMOS image sensor 500 illustrated in FIG. 6 includes the blue photo-sensing device 50B and the red photo-sensing device 50R stacked together, and does not include a color filter layer such as the color filter layer 70 illustrated in FIG. 5. The blue photo-sensing device 50B and the red photo-sensing device 50R are electrically connected to the charge storage 55, and the information of the charge storage 55 may be transferred by the transmission transistor (not shown). The blue photo-sensing device 50B and the red photo-sensing device 50R may be configured to selectively absorb light in each wavelength region depending on a stack depth.

As described above, the organic photoelectric devices selectively absorbing light in a green wavelength region are stacked together, and the red photo-sensing device and the blue photo-sensing device are stacked together, and thereby a size of an image sensor may be decreased and a down-sized image sensor may be realized. As described above, the organic photoelectric device 100 has improved green wavelength selectivity, and crosstalk caused by unnecessary absorption of light in a wavelength region, except the green wavelength region, may be decreased while increasing sensitivity.

In FIG. 6, the organic CMOS image sensor 500 includes the organic photoelectric device 100 of FIG. 1, but may alternatively include the organic photoelectric device 200 of FIG. 2.

Figure 7:
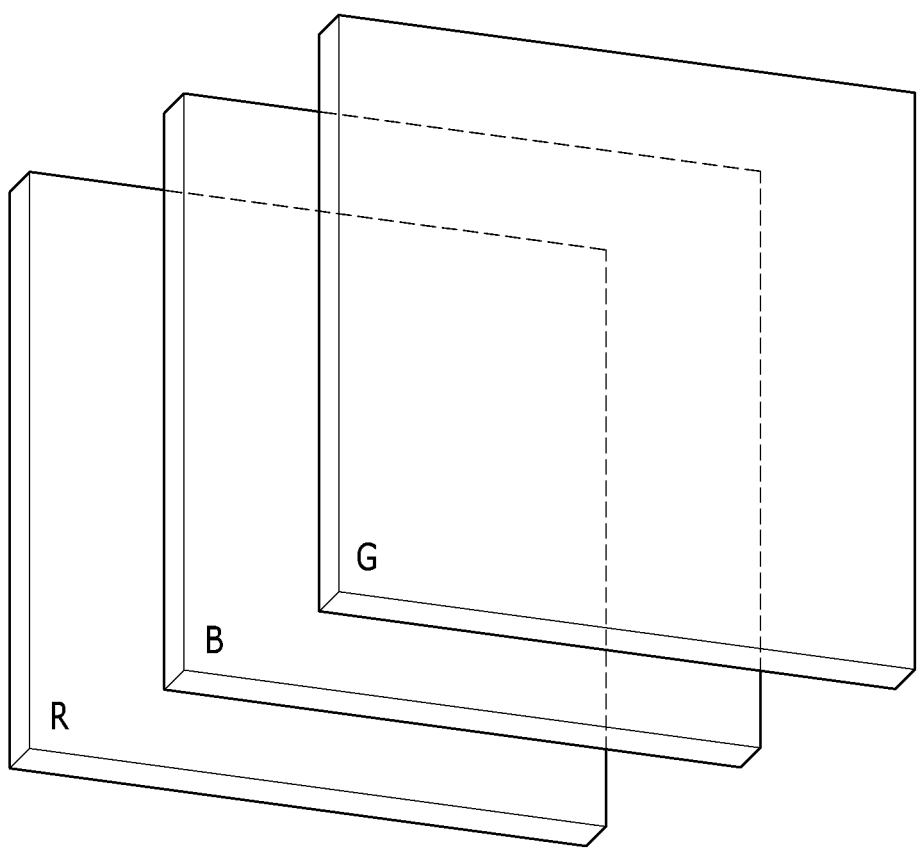
FIG. 7 is a schematic view showing an organic CMOS image sensor according to example embodiments.

FIG. 7 is a schematic view showing an organic CMOS image sensor, according to example embodiments.

Referring to FIG. 7, the organic CMOS image sensor according to various embodiments includes a green photoelectric device (G) configured to selectively absorb light in a green wavelength region, a blue photoelectric device (B) configured to selectively absorb light in a blue wavelength region, and a red photoelectric device (R) configured to selectively absorb light in a red wavelength region, arranged in a stacked configuration.

In the drawing, the red photoelectric device (R), the blue photoelectric device (B), and the green photoelectric device (G) are sequentially stacked, but the stack order may be changed without limitation.

The green photoelectric device may be the same as or similar to the above organic photoelectric device 100, the blue photoelectric device may include electrodes facing each other and an active layer interposed therebetween and including an organic material configured to selectively absorb light in a blue wavelength region, and the red photoelectric device may include electrodes facing each other and an active layer interposed therebetween and including an organic material configured to selectively absorb light in a red wavelength region.

As described above, the organic photoelectric device selectively absorbing light in a green wavelength region, the organic photoelectric device selectively absorbing light in a red wavelength region, and the organic photoelectric device selectively absorbing light in a blue wavelength region are in a stacked configuration, and thereby a size of an image sensor may be decreased, and as a result a down-sized image sensor may be realized.

The image sensor according to the various example embodiments may be used in various electronic devices such as, for example, a mobile phone and/or a digital camera, but is not limited thereto.

Hereinafter, the example embodiments are illustrated in more detail with reference to examples. However, these examples do not limit the scope of the various embodiments.

SYNTHESIS EXAMPLES

Synthesis Example 1

A compound according to Chemical Formula 1a is synthesized according to Reaction Scheme 1.

[Chemical Formula 1a]

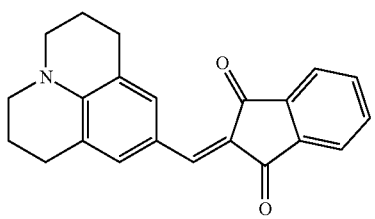

[Reaction Scheme 1]

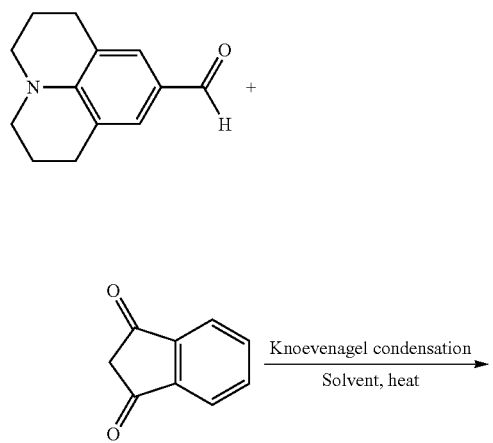

A desired compound represented by Chemical Formula 1a is obtained by stirring 1,2,3,5,6,7-hexahydropyrido[3,2,1-ij]quinoline-9-carbaldehyde (4.02 g) and a compound of 1H-indene-1,3(2H)-dione (2.92 g) in an ethanol solvent (150 ml) at 50° C. for 4 hours under a reflux, filtering a solid obtained therefrom, chemically purifying it with column chromatography, and recrystallizing it (its yield=79%).

MALDI-TOF: 328.93 (M+), 329.14 (calculated for $C_{22}H_{19}NO_2$).

Synthesis Example 2

A desired compound represented by Chemical Formula 1b is obtained according to Reaction Scheme 2.

[Chemical Formula 1b]

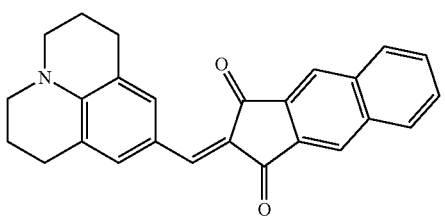

[Reaction Scheme 2]

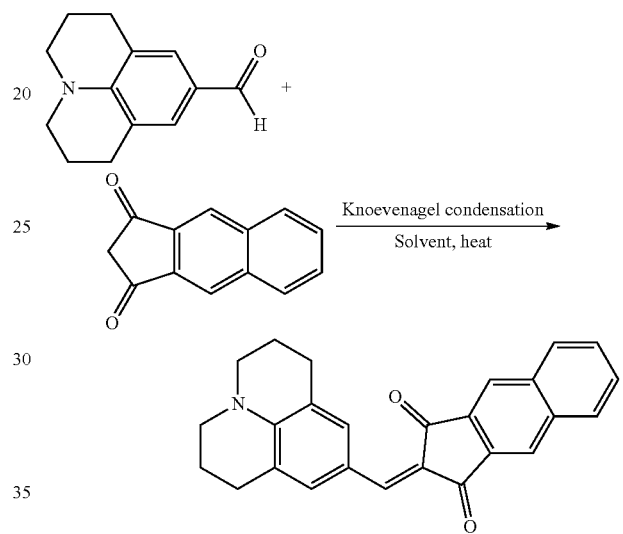

The compound represented by Chemical Formula 1b is obtained by stirring 1,2,3,5,6,7-hexahydropyrido[3,2,1-ij]quinoline-9-carbaldehyde (4.02 g) and 1H-cyclopenta[b]naphthalene-1,3(2H)-dione (3.92 g) in an ethanol solvent (150 ml) at 50° C. under a reflux for 4 hours, filtering a solid obtained therefrom, chemically purifying it with column chromatography, and recrystallizing it (its yield=74%).

MALDI-TOF: 378.96 (Mt), 379.16 (calculated for $C_{26}H_{21}NO_2$).

Synthesis Example 3

A desired compound represented by Chemical Formula 1c is obtained according to Reaction Scheme 3.

[Chemical Formula 1c]

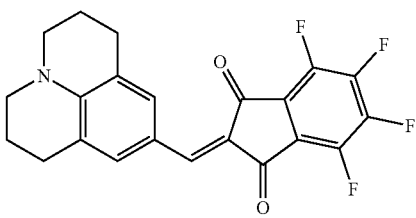

[Reaction Scheme 3]

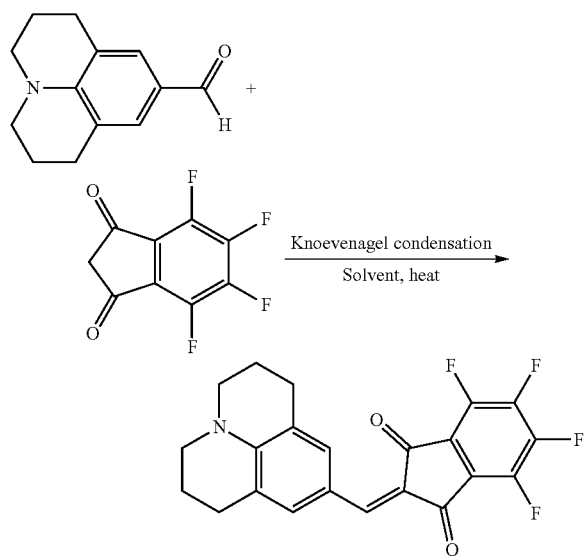

The compound represented by Chemical Formula 1c is obtained by stirring 1,2,3,5,6,7-hexahydropyrido[3,2,1-ij]quinoline-9-carbaldehyde (4.02 g) and 4,5,6,7-tetrafluoro-1H-indene-1,3(2H)-dione (4.36 g) in an ethanol solvent (150 ml) at 50° C. under a reflux for 4 hours, filtering a solid obtained therefrom, chemically purifying it with column chromatography, and recrystallizing it (its yield=79%).

MALDI-TOF: 409.06 (M+), 401.10 (calculated for $C_{22}H_{15}F_4NO_2$).

Synthesis Example 4

A desired compound represented by Chemical Formula 1d is obtained according to Reaction Scheme 4.

[Chemical Formula 1d]

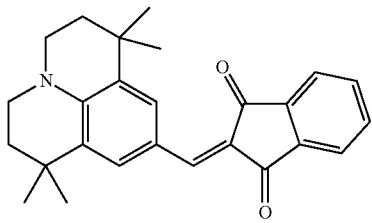

[Reaction Scheme 4]

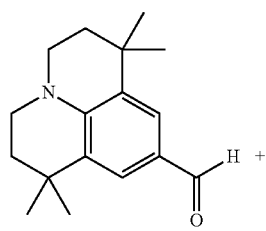

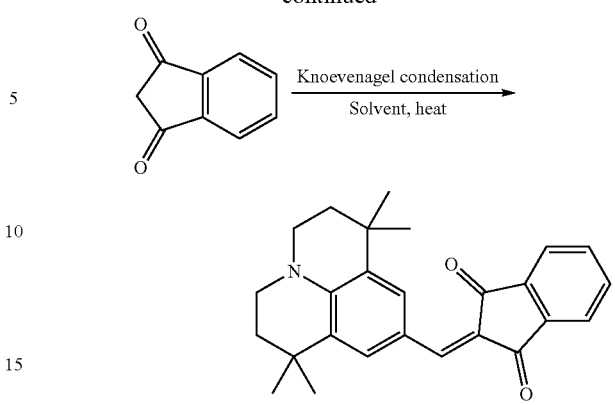

The compound represented by Chemical Formula 1d is obtained by stirring 1,1,7,7-tetramethyl-1,2,3,5,6,7-hexahydropyrido[3,2,1-ij]quinoline-9-carbaldehyde (5.14 g) and 1H-indene-1,3(2H)-dione (2.92 g) in an ethanol solvent (150 ml) at 50° C. under a reflux for 4 hours, filtering a solid obtained therefrom, chemically purifying it with column chromatography, and recrystallizing it (its yield=87%).

MALDI-TOF: 384.18 (M+), 385.20 (calculated for $C_{26}H_{27}NO_2$).

Synthesis Example 5

A desired compound represented by Chemical Formula 1e is obtained according to Reaction Scheme 5.

[Chemical Formula 1e]

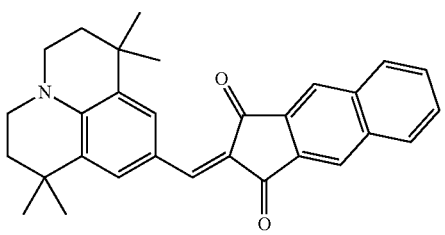

[Reaction Scheme 5]

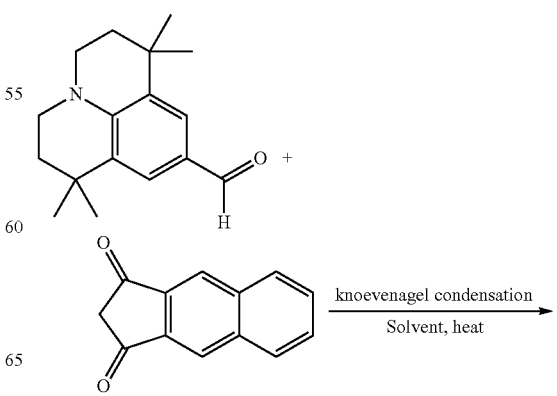

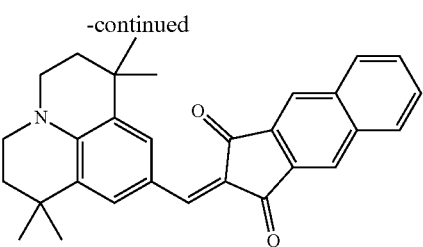

The compound represented by Chemical Formula 1e is obtained by stirring 1,1,7,7-tetramethyl-1,2,3,5,6,7-hexahydropyrido[3,2,1-ij]quinoline-9-carbaldehyde (5.14 g) and 1H-cyclopenta[b]naphthalene-1,3(2H)-dione (3.92 g) in an ethanol solvent (150 ml) at 50° C. under a reflux for 4 hours, filtering a solid obtained therefrom, chemically purifying it with column chromatography, and recrystallizing it (its yield=78%).

MALDI-TOF: 435.21 (M+), 435.22 (calculated for $C_{30}H_{29}NO_2$).

Synthesis Example 6

A desired compound represented by Chemical Formula 1f is obtained according to Reaction Scheme 6.

[Chemical Formula 1f]

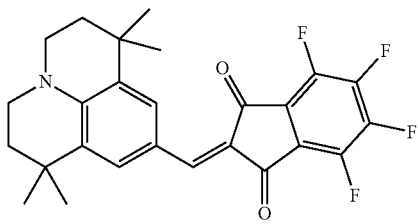

[Reaction Scheme 6]

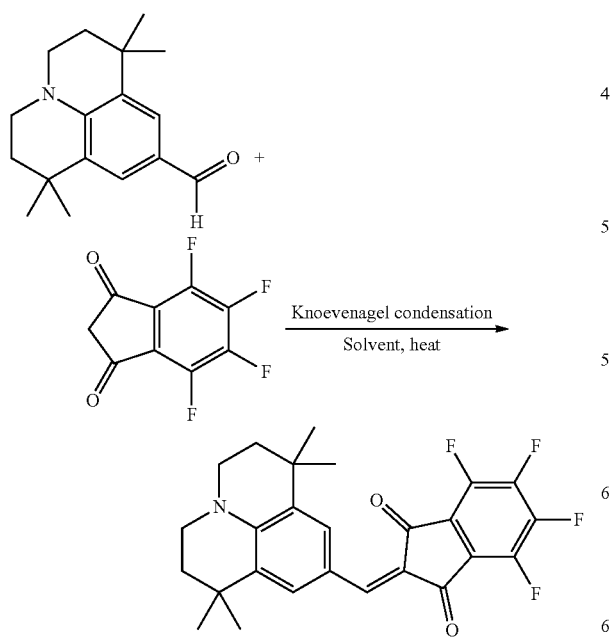

The compound represented by Chemical Formula 1f is obtained by stirring 1,1,7,7-tetramethyl-1,2,3,5,6,7-hexahydropyrido[3,2,1-ij]quinoline-9-carbaldehyde (5.14 g) and 4,5,6,7-tetrafluoro-1H-indene-1,3(2H)-dione (4.36 g) in an ethanol solvent (150 ml) at 50° C. under a reflux for 4 hours, filtering a solid obtained therefrom, chemically purifying it with column chromatography, and recrystallizing it (its yield=74%).

MALDI-TOF: 457.17 (M+), 457.17 (calculated for $C_{26}H_{23}F_4NO_2$).

Synthesis Example 7

A desired compound represented by Chemical Formula 1g is obtained according to Reaction Scheme 7.

[Chemical Formula 1g]

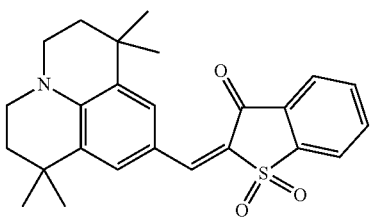

[Reaction Scheme 7]

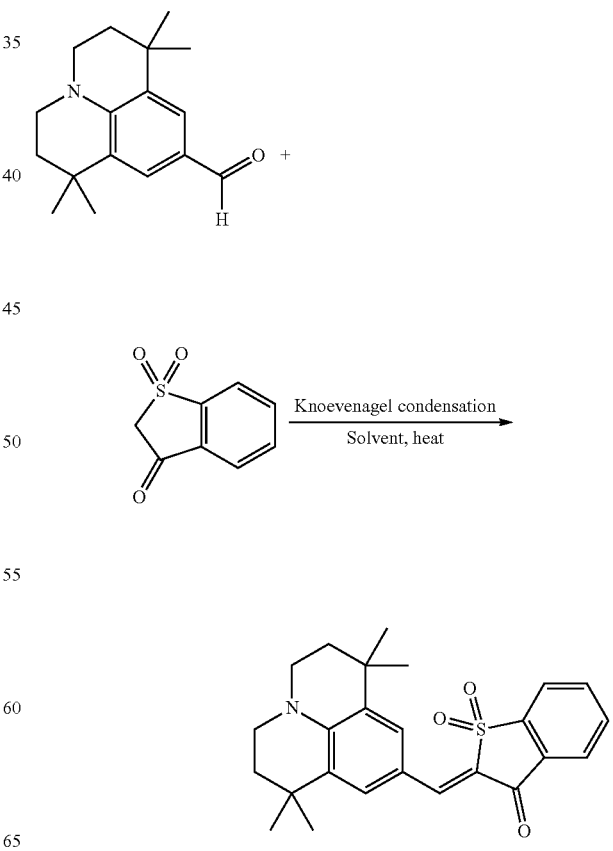

The compound represented by Chemical Formula 1g is obtained by stirring 1,1,7,7-tetramethyl-1,2,3,5,6,7-hexahydropyrido[3,2,1-ij]quinoline-9-carbaldehyde (5.14 g) and benzo[b]thiophen-3(2H)-one 1,1-dioxide (3.64 g) in an ethanol solvent (150 ml) at 50° C. under a reflux for 4 hours, filtering a solid obtained therefrom, chemically purifying it, and recrystallizing it (its yield=82%).

MALDI-TOF: 421.16 (M+), 421.17 (calculated for $C_{25}H_{27}NO_3S$).

Comparative Synthesis Example 1

A desired compound represented by Chemical Formula 1h is obtained as published in EP 2259359 A2.

[Chemical Formula 1h]

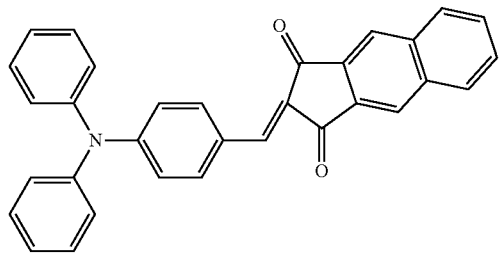

Comparative Synthesis Example 2

A desired compound represented by Chemical Formula 1i is obtained as published in EP 2259359 A2.

[Chemical Formula 1i]

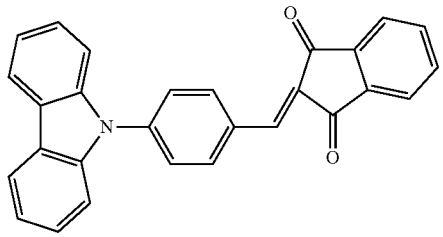

Comparative Synthesis Example 3

A desired compound represented by Chemical Formula 1j is obtained as published in WO 2014-054255 A1.

[Chemical Formula 1j]

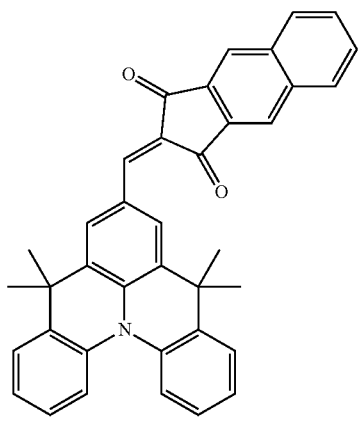

Light Absorption Characteristics of Compounds of Synthesis Examples 1 to 7 and Comparative Synthesis Examples 1 to 3

Light absorption characteristics are evaluated in both a solution state and in a thin film state, as discussed below.

Light absorption characteristics in the solution state are evaluated by respectively dissolving each compound according to Synthesis Examples 1 to 7 and Comparative Synthesis Examples 1 to 3 in an amount of $1.0 \times 10^{-5}$ mol/L in toluene. A maximum absorption wavelength in the solution state is calculated by using a UV-2450 UV-visible spectrophotometer (Shimadzu Co.).

Light absorption characteristics in the thin film state are measured by thermally depositing each compound according to Synthesis Example 1 to 7 and Comparative Synthesis Example 1 to 3 under a high vacuum ($<10^{-7}$ Torr) at a speed of 0.5-1.0 Å/s to form a 70 nm-thick thin film and measuring a maximum absorption wavelength in the thin film by using UV-2450 UV-visible spectrophotometer (Shimadzu Co.).

Each compound according to Synthesis Examples 1 to 7 and Comparative Synthesis Examples 1 to 3 and C60 in a volume ratio of 1:1 are codeposited to form a 70 nm-thick thin film, and the thin film is radiated by ultraviolet-visible ray (UV-Vis) to measure an extinction coefficient with Cary 5000 UV spectrometer (Varian Medical Systems).

The results are provided in Table 1 below.

Figure 8:
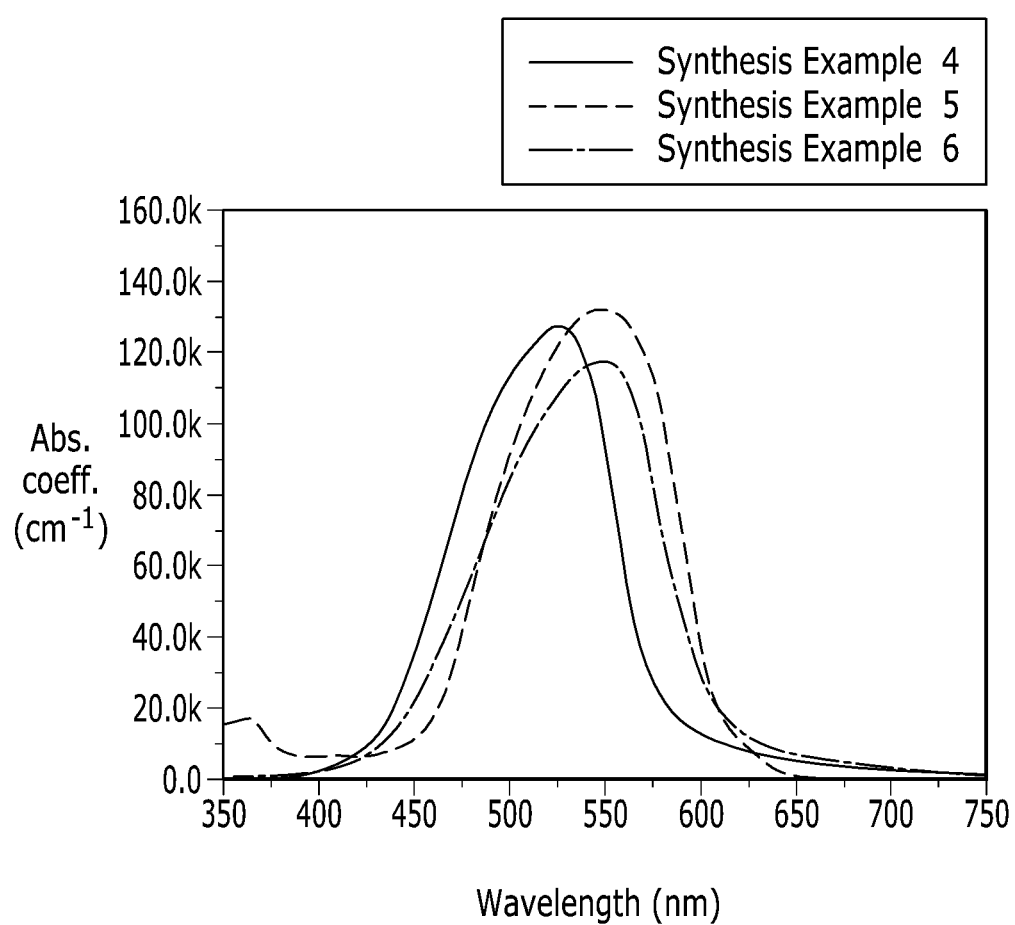
FIG. 8 is a graph showing a light absorption curved line of the compounds according to Synthesis Examples 4 to 6 in a thin film state.

The light absorption curves of the compounds according to Synthesis Examples 4 to 6 in a thin film state are provided in FIG. 8.

Thermal Stability of Compounds of Synthesis Examples 1 to 7 and Comparative Synthesis Examples 1 to 3

Thermal stability of the compounds of Synthesis Examples 1 to 7 and Comparative Synthesis Examples 1 to 3 is evaluated by measuring their melting temperatures and thermal decomposition temperatures. The thermal decomposition temperature ($T_d$) is a temperature at which a compound starts to be decomposed and thus, does not maintain its intrinsic molecular structure but is transformed. In general, atoms in a molecule consisting of a compound are volatilized and lost into the air or vacuum at greater than or equal to a thermal decomposition temperature, and thus, the thermal decomposition temperature may be regarded as a temperature at which initial weight of the compound starts to be decreased by heat. Herein, a thermal gravimetric analysis (TGA) method is used to measure the thermal decomposition temperature. The results are shown in Table 1.

TABLE 1

| | $\lambda_{max}$ (nm) | | FWHM (nm) | | Extinction coefficient (thin film, ×10⁴ cm⁻¹) | Energy level | | $T_m$ (° C.) | $T_d$ (° C.) |
|---|---|---|---|---|---|---|---|---|---|
| | solution | thin film | solution | thin film | | HOMO (eV) | LUMO (eV) | | |
| Synthesis Example 1 | 516 | 531 | 48 | 83 | 8.5 | 5.36 | 3.24 | 240 | 223 |
| Synthesis Example 2 | 544 | 569 | 51 | 89 | 8.7 | 5.54 | 3.51 | 227 | 225 |
| Synthesis Example 3 | 528 | 540 | 44 | 95 | 18.0 | 5.60 | 3.57 | — | 227 |
| Synthesis Example 4 | 513 | 526 | 46 | 90 | 19.7 | 5.38 | 3.24 | 198 | 258 |
| Synthesis Example 5 | 545 | 550 | 48 | 100 | 22.6 | 5.54 | 3.53 | 250 | 266 |
| Synthesis Example 6 | 526 | 547 | 47 | 97 | 20.0 | 5.59 | 3.54 | — | 267 |
| Synthesis Example 7 | 513 | 526 | 47 | 98 | 15.0 | 5.49 | 3.35 | 205 | 265 |
| Comparative Synthesis Example 1 | 515 | 513 | 69 | 103 | 10.5 | 5.32 | 3.18 | — | 282 |
| Comparative Synthesis Example 2 | 441 | 452 | 78 | 88 | 6.15 | 5.85 | 3.55 | 240 | 288 |
| Comparative Synthesis Example 3 | 534 | 558 | 79 | 112 | 5.4 | 5.64 | 3.06 | 310 | — |

Referring to Table 1, the compounds according to Synthesis Examples 1 to 7 in the thin film state respectively show a maximum absorption wavelength ($\lambda_{max}$) in a range of 526 nm to 569 nm and a full width at half maximum (FWHM) in a range of 83 nm to 100 nm and thus good selective absorption about light in a green wavelength region. In addition, as shown in FIG. 8, the compounds have similar or same light absorption curves to a Gaussian distribution.

On the contrary, the compound according to Comparative Synthesis Example 1 shows a maximum absorption wavelength in the middle of blue wavelength and green wavelength, the compound according to Comparative Synthesis Example 2 shows a maximum absorption wavelength in a blue wavelength region, and the compound according to Comparative Synthesis Example 3 shows a maximum absorption wavelength in a green wavelength region but a wide full width at half maximum (FWHM) and a low extinction coefficient.

In addition, the results in Table 1 show that the compounds according to Synthesis Examples 1 to 7 have improved thermal stability from high melting temperatures and/or high decomposition temperatures, and thus may be appropriately used in a deposition process.

Organic Photoelectric Device

Example 1

An about 150 nm-thick anode is formed by sputtering ITO on a glass substrate, and then, a 20 nm-thick molybdenum oxide ($MoO_x$, $0<x\leq3$) thin film as a charge auxiliary layer is formed thereon. Subsequently, an 85 nm-thick active layer is formed by codepositing the compound of Synthesis Example 1 (a p-type semiconductor compound) and C60 (an n-type semiconductor compound) in a thickness (volume) ratio of 1:1 on the molybdenum oxide ($MoO_x$) thin film. Then, a 7 nm-thick cathode is formed by sputtering ITO on the active layer, manufacturing an organic photoelectric device.

Examples 2 to 7

Each organic photoelectric device is manufactured according to the same method as in Example 1 above, except for respectively using the compounds according to Synthesis Example 2 to 7 (a p-type semiconductor compound) instead of the compound according to Synthesis Example 1 (a p-type semiconductor compound).

Comparative Examples 1 to 3

Each organic photoelectric device is manufactured according to the same method as in Example 1, except for respectively using the compounds (a p-type semiconductor compound) according to Comparative Synthesis Example 1 to 3 instead of the compound according to Synthesis Example 1 (a p-type semiconductor compound).

External Quantum Efficiency (EQE)

The organic photoelectric devices according to Examples 1 to 7 and Comparative Examples 1 to 3 are evaluated with respect to external quantum efficiency (EQE) in relation to wavelength and voltage.

The external quantum efficiency is measured by using an Incident Photo to Charge Carrier Efficiency (IPCE) measurement system (McScience Inc., Korea). First of all, the IPCE measurement system is calibrated by using a Si photodiode (Hamamatsu Photonics K.K., Japan) and the organic photoelectric devices according to Examples 1 to 7 and Comparative Examples 1 to 3 are respectively mounted thereon to measure the external quantum efficiency thereof at wavelengths ranging from about 300 to about 700 nm.

Figure 9:
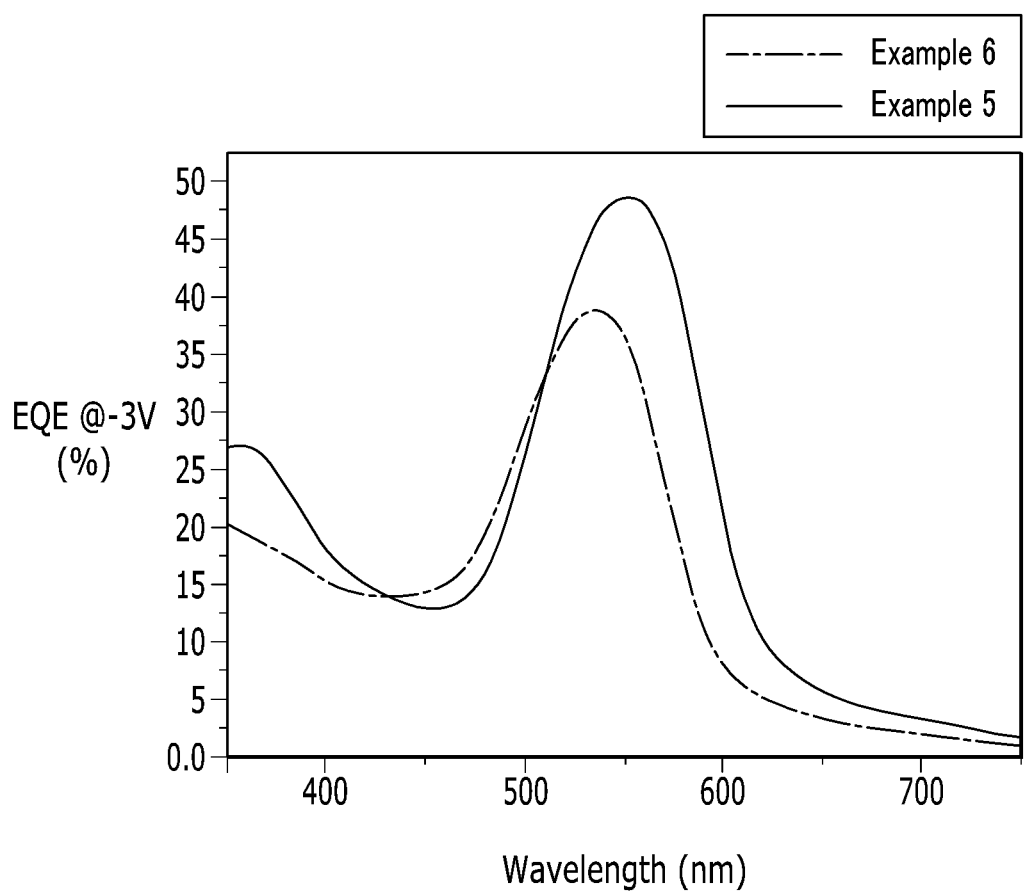
FIG. 9 is a graph showing external quantum efficiency (EQE) depending on a wavelength of the organic photoelectric devices according to Example 5 and Example 6.
Figure 10:
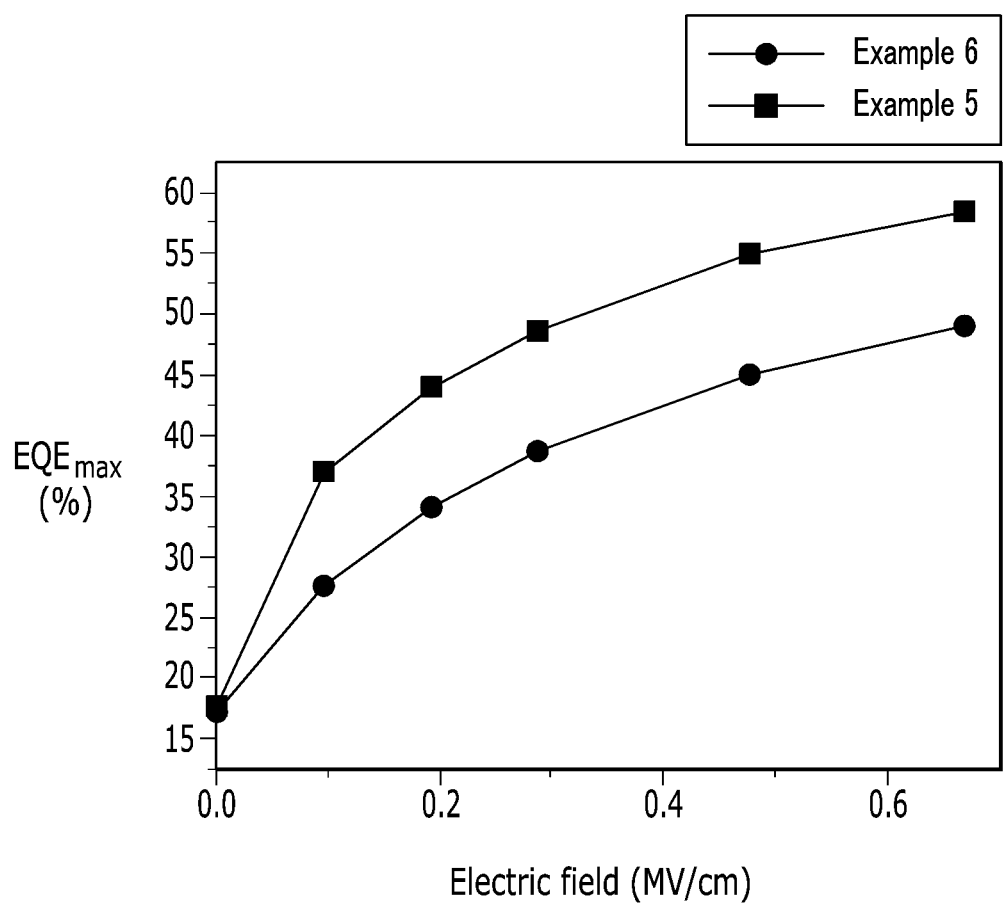
FIG. 10 shows external quantum efficiency ($EQE_{max}$) depending on an applied electric field of the organic photoelectric devices according to Example 5 and Example 6.

FIG. 9 shows external quantum efficiency (EQE) of the organic photoelectric devices according to Examples 5 and 6 with respect to wavelength, and FIG. 10 shows external quantum efficiency (EQE) of the organic photoelectric devices according to Examples 5 and 6 with respect to the electric field applied thereto.

Referring to FIG. 9, the organic photoelectric devices according to Examples 5 and 6 show satisfactory external quantum efficiency ($EQE_{max}$) in a green wavelength region ranging from about 500 nm to 600 nm. In addition, referring to FIG. 10, the organic photoelectric devices according to Examples 5 and 6 show improved external quantum efficiency with respect to the electric field applied thereto.

Crosstalk

The organic photoelectric devices according to Examples 1 to 7 and Comparative Examples 1 to 3 are measured regarding crosstalk. The organic photoelectric devices according to Examples 1 to 7 and Comparative Examples 1 to 3 are respectively stacked on a red silicon photodiode and a blue silicon photodiode, and photocurrents (electric signals) obtained by applying a voltage thereto are measured. The measured photocurrents are converted into EQE. The measurement result of Example 5 is illustrated in FIG. 11.

Figure 11:
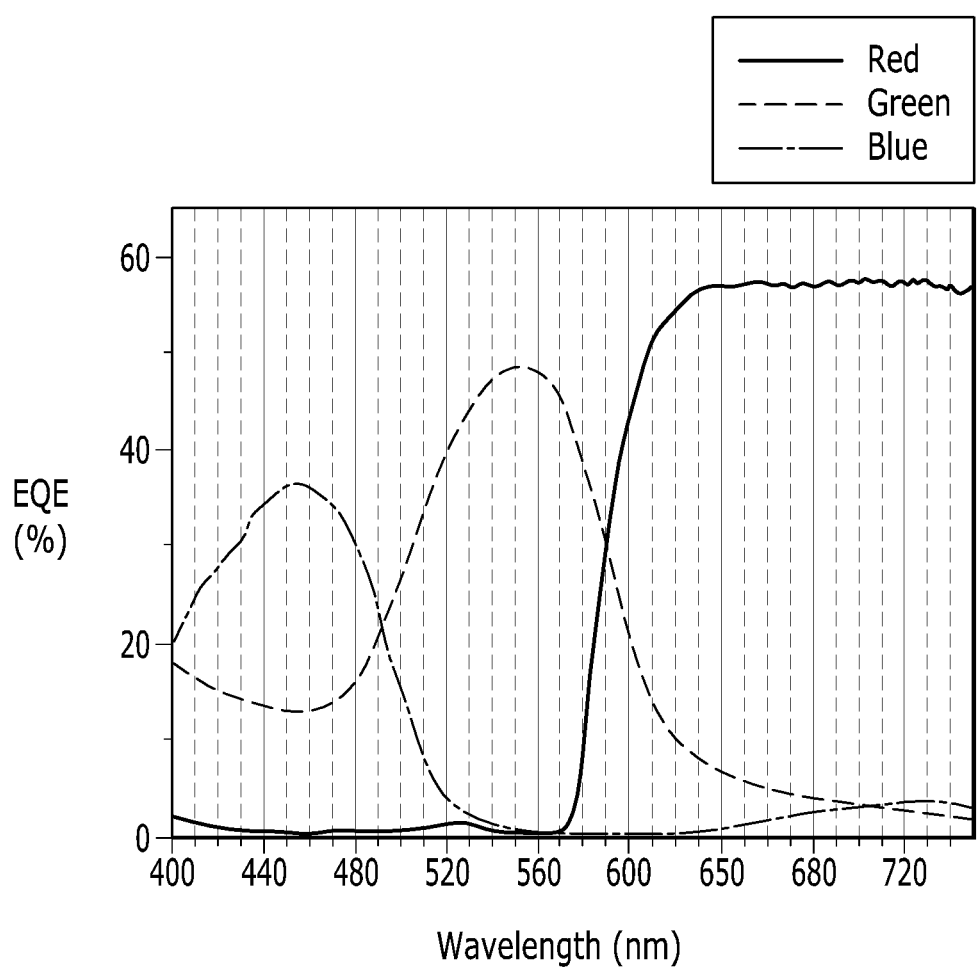
FIG. 11 is a graph showing a crosstalk of the organic photoelectric device according to Example 5.

As shown in FIG. 11, the electric signal of the organic photoelectric device according to Example 5 does not show a noticeable overlap between the red and blue electric signals in the range of 500 nm to 600 nm. Accordingly, crosstalk does not substantially occur.

While this disclosure has been described in connection with what is presently considered to be example embodiments, it is to be understood that the embodiments are not limited to the disclosed examples, but, on the contrary, are intended to cover various modifications and equivalent arrangements included within the spirit and scope of the appended claims.

What is claimed is:

1. An image sensor comprising:
   an organic photoelectric device including:
      a first electrode and a second electrode facing each other; and
      an active layer between the first electrode and the second electrode; and
   a semiconductor substrate integrated with at least one photo-sensing device;
   the organic photoelectric device being on the semiconductor substrate;
   wherein the active layer comprises a compound for an organic photoelectric device represented by Chemical Formula 1:

[Chemical Formula 1]

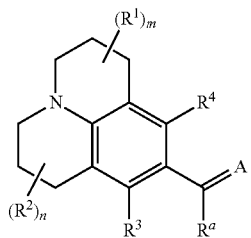

wherein, in Chemical Formula 1,
A is a functional group represented by Chemical Formula 1-1 or 1-2,
$R^1$ to $R^4$ are independently one of hydrogen, a substituted or unsubstituted C1 to C30 alkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C2 to C30 heterocycloalkyl group, and a combination thereof, or two adjacent functional groups of $R^1$ to $R^4$ are linked to each other to form a cycloalkyl group or a heterocycloalkyl group fused with a julolidinyl group,
m and n are independently an integer ranging from 0 to 6, and
$R^a$ is one of hydrogen, a substituted or unsubstituted C1 to C10 alkyl group, a substituted or unsubstituted C1 to C10 haloalkyl group, a halogen, a cyano group (—CN), and a combination thereof,

[Chemical Formula 1-1]

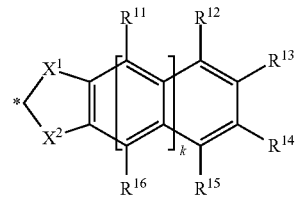

[Chemical Formula 1-2]

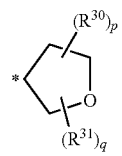

wherein, in Chemical Formulae 1-1 and 1-2,
an asterisk (*) indicates a bonding position with a methine group of Chemical Formula 1,
$X^1$ and $X^2$ are each independently —C($R^{22}$)($R^{23}$)— (wherein $R^{22}$ and $R^{23}$ are independently one of hydrogen, a substituted or unsubstituted C1 to C10 alkyl group, a substituted or unsubstituted C1 to C10 haloalkyl group, a halogen, a cyano group, a cyano-containing group, and a combination thereof), —C(=C($R^{24}$)($R^{25}$))— (wherein $R^{24}$ and $R^{25}$ are independently one of a substituted or unsubstituted C1 to C10 alkyl group, a substituted or unsubstituted C1 to C10 haloalkyl group, a halogen, a cyano group (—CN), a cyano-containing group, and a combination thereof), an indanone group, an indandione group, —C(=O)—, —S(=O)$_2$—, and a combination thereof,
$R^{11}$ to $R^{16}$ are independently one of hydrogen, a substituted or unsubstituted C1 to C10 alkyl group, a substituted or unsubstituted C1 to C10 haloalkyl group, a halogen, a cyano group (—CN), a cyano-containing group, and a combination thereof,
k is an integer of 0 or 1,
$R^{30}$ is one of a halogen, a cyano group (—CN), a cyano-containing group, and a combination thereof,
$R^{31}$ is one of hydrogen, a substituted or unsubstituted C1 to C10 alkyl group, a substituted or unsubstituted C1 to C10 haloalkyl group, a halogen, a cyano group (—CN), a cyano-containing group, and a combination thereof,
p is an integer ranging from 1 to 5, q is an integer ranging from 0 to 5, and p+q is an integer of less than or equal to 5.

2. The image sensor of claim 1, wherein the compound comprises one aromatic ring in the fused ring moiety including a julolidinyl group of Chemical Formula 1.

3. The image sensor of claim 1, wherein the compound comprises 5 to 7 rings.

4. The compound image sensor of claim 1, wherein the compound has a maximum absorption wavelength ($\lambda_{max}$) of about 500 nm to about 600 nm in a thin film state.

5. The image sensor of claim 1, wherein the compound has a maximum absorption wavelength ($\lambda_{max}$) of about 520 nm to about 570 nm in a thin film state.

6. The image sensor of claim 1, wherein a light absorption curve of the compound has a full width at half maximum (FWHM) of about 50 nm to about 100 nm in a thin film state.

7. The image sensor of claim 1, wherein $X^1$ and $X^2$ of Chemical Formula 1-1 are independently —C($R^{22}$)($R^{23}$)— (wherein $R^{22}$ and $R^{23}$ are independently one of —F, —Cl, —Br, —I, a cyano group, a cyano-containing group, and a combination thereof), —C(=C($R^{24}$)($R^{25}$))— (wherein $R^{24}$ and $R^{25}$ are independently one of —F, —Cl, —Br, —I, a cyano group (—CN), a cyano-containing group, and a combination thereof), —C(=O)—, —S(=O)$_2$—, and a combination thereof.

8. The image sensor of claim 1, wherein A of Chemical Formula 1 comprises a functional group represented by Chemical Formula 1A:

[Chemical Formula 1A]

(1)

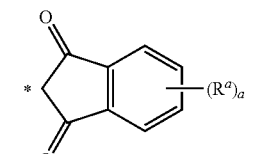

(2)

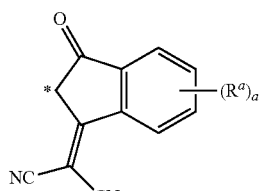

(3)

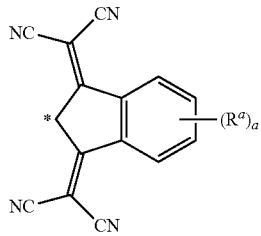

(4)

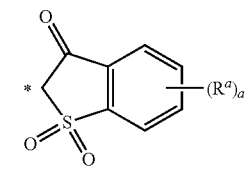

(5)

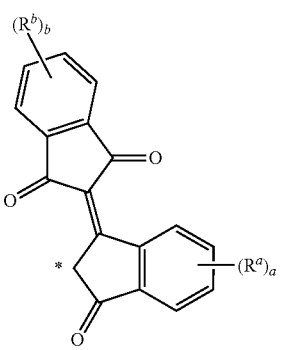

(6)

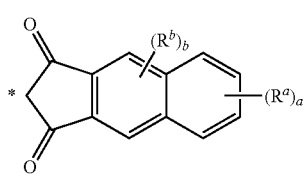

(7)

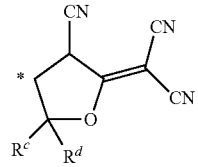

wherein the asterisk (*) indicates a bonding position with a methine group of Chemical Formula 1, $R^a$, $R^b$, $R^c$ and $R^d$ are independently one of hydrogen, a substituted or unsubstituted C1 to C6 alkyl group, a substituted or unsubstituted C1 to C6 haloalkyl group, a halogen, a cyano group (—CN), a cyano-containing group, and a combination thereof, a is an integer ranging from 0 to 4, and b is an integer ranging from 0 to 2.

9. The image sensor of claim 1, wherein the active layer comprises the compound and C60 in a volume ratio of about 0.9:1 to about 1.1:1 and has an extinction coefficient that is greater than or equal to about $8.0 \times 10^4$ cm-1.

10. The image sensor of claim 1, wherein the photo-sensing device comprises a first photo-sensing device configured to sense light in a blue wavelength region and a second photo-sensing device configured to sense light in a red wavelength region, and the first photo-sensing device and the second photo-sensing device are in a vertical stacking configuration on the semiconductor substrate.

11. The image sensor of claim 1, wherein a green photoelectric device of the organic photoelectric device, a blue photoelectric device configured to selectively absorb light in a blue wavelength region, and a red photoelectric device configured to selectively absorb light in a red wavelength region, are in a stacked configuration.

12. An electronic device comprising the image sensor of claim 1.

13. The image sensor of claim 1, wherein the active layer further comprises an n-type semiconductor compound.

14. The image sensor of claim 13, wherein the n-type semiconductor compound comprises at least one of sub-phthalocyanine or a sub-phthalocyanine derivative, fullerene or a fullerene derivative, and thiophene or a thiophene derivative.

15. The image sensor of claim 1, wherein the active layer is an intrinsic layer comprising the compound represented by Chemical Formula 1.

16. The image sensor of claim 15, wherein the active layer further comprises at least one of a p-type layer on one side of the intrinsic layer and an n-type layer on an other side of the intrinsic layer.

17. The image sensor of claim 1, wherein the active layer further comprises a p-type semiconductor compound configured to selectively absorb green light.

18. The image sensor of claim 17, wherein the p-type semiconductor compound is represented by Chemical Formula 6:

[Chemical Formula 6]

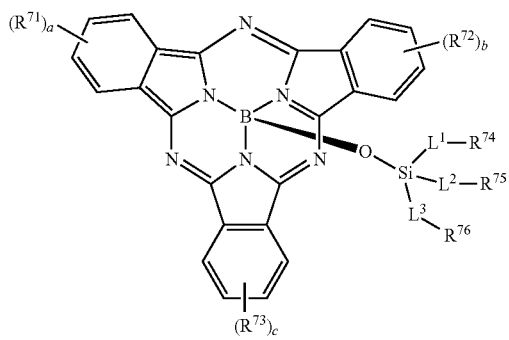

wherein, in Chemical Formula 6,
$R^{71}$ to $R^{73}$ are independently one of hydrogen, a substituted or unsubstituted C1 to C30 aliphatic hydrocarbon group, a substituted or unsubstituted C6 to C30 aromatic hydrocarbon group, a substituted or unsubstituted C2 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group, or a combination thereof, or $R^{71}$ to $R^{73}$ are linked to each other to form a fused ring, $L^1$ to $L^3$ are independently a single bond, a substituted or unsubstituted C1 to C30 alkylene group, a substituted or unsubstituted C6 to C30 arylene group, a divalent substituted or unsubstituted C2 to C30 heterocyclic group, or a combination thereof, $R^{74}$ to $R^{76}$ are independently a substituted or unsubstituted C1 to C30 alkyl group, a substituted or unsubstituted C6 to C30 aryl group, a substituted or unsubstituted C2 to C30 heterocyclic group, a substituted or unsubstituted C1 to C30 alkoxy group, a substituted or unsubstituted amine group, a substituted or unsubstituted silyl group or a combination thereof, and a, b and c are independently an integer of 0 to 4.

19. The image sensor of claim 1, further comprising a semiconductor substrate integrated with a plurality of first photo-sensing devices configured to sense light in a blue wavelength region, and a plurality of second photo-sensing devices configured to sense light in a red wavelength region, and the organic photoelectric device on the semiconductor substrate is configured to selectively absorb light in a green wavelength region.

20. The image sensor of claim 19, further comprising a color filter layer between the semiconductor substrate and the organic photoelectric device, a blue filter configured to selectively transmit light in a blue wavelength region, and a red filter configured to selectively transmit light in a red wavelength region.

21. An image sensor comprising:
an organic photoelectric device including:
a first electrode and a second electrode facing each other; and
an active layer between the first electrode and the second electrode; and
a semiconductor substrate integrated with at least one photo-sensing device;
the organic photoelectric device being on the semiconductor substrate;
wherein the active layer comprises a compound for an organic photoelectric device represented by Chemical Formula 2 and having a maximum absorption wavelength ($\lambda_{max}$) of about 500 nm to about 600 nm in a thin film state:

[Chemical Formula 2]

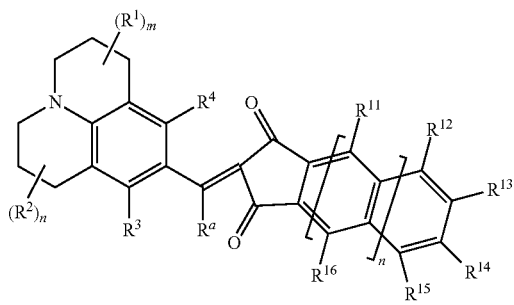

wherein, in Chemical Formula 2,
$R^1$ to $R^4$ are independently one of hydrogen, a substituted or unsubstituted C1 to C30 alkyl group, a substituted or unsubstituted C6 to C30 aryl group, a substituted or unsubstituted C2 to C30 heteroaryl group, a substituted or unsubstituted C3 to C30 cycloalkyl group substituted or unsubstituted C2 to C30 heterocycloalkyl group, and a combination thereof, or
two adjacent functional groups of $R^1$ to $R^4$ linked to each other to form a cycloalkyl group or a heterocycloalkyl group fused with a julolidinyl group,
m and n are independently an integer ranging from 0 to 6,
$R^a$ is one of hydrogen, a substituted or unsubstituted C1 to C10 alkyl group, a substituted or unsubstituted C1 to C10 haloalkyl group, a halogen, a cyano group (—CN), and a combination thereof,
$R^{11}$ to $R^{16}$ are independently one of hydrogen, a substituted or unsubstituted C1 to C10 alkyl group, a substituted or unsubstituted C1 to C10 haloalkyl group, a halogen, a cyano group (—CN), a cyano-containing group, and a combination thereof, and
n is an integer of 0 or 1.

22. The image sensor of claim 21, wherein the compound comprises one aromatic ring in the fused ring moiety including a julolidinyl group of Chemical Formula 1.

23. The image sensor of claim 21, wherein the compound comprises 5 to 7 rings.

24. The image sensor of claim 21, wherein the compound has a maximum absorption wavelength ($\lambda_{max}$) of about 520 nm to about 570 nm in a thin film state.

* * * * *